United States Patent
Noerpel et al.

(10) Patent No.: US 12,023,392 B2
(45) Date of Patent: Jul. 2, 2024

(54) ADDITIVE MANUFACTURING PROCESS

(71) Applicant: DENTSPLY DETREY GMBH, Constance (DE)

(72) Inventors: Stephanie Noerpel, Constance (DE); Thomas Tigges, Constance (DE); Uwe Walz, Constance (DE); Christoph Weber, Constance (DE)

(73) Assignee: DENTSPLY SIRONA INC., York, PA (US)

( * ) Notice: Subject to any disclaimer, the term of this patent is extended or adjusted under 35 U.S.C. 154(b) by 352 days.

(21) Appl. No.: 17/296,700

(22) PCT Filed: Nov. 27, 2019

(86) PCT No.: PCT/EP2019/082753
§ 371 (c)(1),
(2) Date: May 25, 2021

(87) PCT Pub. No.: WO2020/109390
PCT Pub. Date: Jun. 4, 2020

(65) Prior Publication Data
US 2022/0031576 A1    Feb. 3, 2022

(30) Foreign Application Priority Data

Nov. 27, 2018   (EP) ..................... 18208698

(51) Int. Cl.

| | |
|---|---|
| *B33Y 10/00* | (2015.01) |
| *A61C 5/77* | (2017.01) |
| *A61K 6/17* | (2020.01) |
| *A61K 6/77* | (2020.01) |
| *A61K 6/887* | (2020.01) |
| *B33Y 70/10* | (2020.01) |
| *B33Y 80/00* | (2015.01) |
| *B29C 64/112* | (2017.01) |
| *B29C 64/118* | (2017.01) |
| *B29C 64/259* | (2017.01) |
| *B29K 509/08* | (2006.01) |

(52) U.S. Cl.
CPC .............. *A61K 6/77* (2020.01); *A61C 5/77* (2017.02); *A61K 6/17* (2020.01); *A61K 6/887* (2020.01); *B33Y 70/10* (2020.01); *B33Y 80/00* (2014.12); *B29C 64/112* (2017.08); *B29C 64/118* (2017.08); *B29C 64/259* (2017.08); *B29K 2509/08* (2013.01); *B33Y 10/00* (2014.12)

(58) Field of Classification Search
None
See application file for complete search history.

(56) References Cited

U.S. PATENT DOCUMENTS

| | | | |
|---|---|---|---|
| 4,298,738 A | 11/1981 | Lechtken | |
| 4,324,744 A | 4/1982 | Echtken | |
| 4,385,109 A | 5/1983 | Lechtken | |
| 4,814,362 A | 3/1989 | Billington | |
| 5,154,762 A | 10/1992 | Mitra | |
| 5,318,929 A | 6/1994 | Jana | |
| 5,360,770 A | 11/1994 | Chadwick | |
| 5,501,727 A | 3/1996 | Wang | |
| 5,545,676 A | 8/1996 | Palazzotto | |
| 2002/0167100 A1* | 11/2002 | Moszner | A61K 6/887 264/16 |
| 2004/0079258 A1 | 4/2004 | Hoescheler | |
| 2017/0321037 A1 | 11/2017 | Mason | |
| 2018/0111316 A1 | 4/2018 | Schaufelberger | |

FOREIGN PATENT DOCUMENTS

| | | |
|---|---|---|
| CA | 2371357 A1 | 9/2002 |
| EP | 0173567 A2 | 3/1986 |
| EP | 0969789 A2 | 1/2000 |
| EP | 1252867 A1 | 10/2002 |
| EP | 1911568 A1 | 4/2008 |
| EP | 2705827 A1 | 3/2014 |
| EP | 2727576 A1 | 5/2014 |
| JP | 2002291771 A | 10/2002 |
| JP | 2017538852 A | 12/2017 |
| JP | 2018509321 A | 4/2018 |

(Continued)

OTHER PUBLICATIONS

Japanese Office Action dated Oct. 19, 2021.

(Continued)

*Primary Examiner* — Mohammad M Ameen
(74) *Attorney, Agent, or Firm* — DENTSPLY SIRONA INC.

(57) ABSTRACT

An additive manufacturing process comprising:
  (a) providing a curable composition comprising:
    (i) a filler comprising glassflakes having a diameter $D_{3,99}$ as determined by light scattering in the range of from 5 to 150 μm; and
    (ii) one or more curable compounds;
  (b) controlling an apparatus to form an object by using the curable composition, whereby the curable composition passes a discharge orifice having a minimum diameter $\Phi_{min}$,
wherein the ratio of the minimum diameter of the discharge orifice to the diameter $D_{3,99}$ of the glassflakes ($\Phi_{min}/D_{3,99}$) is in the range of 2 to less than 10; and wherein the median diameter $D_{3,50}$ of the glassflakes is larger than the thickness of the glassflakes.

15 Claims, 1 Drawing Sheet

(56) References Cited

FOREIGN PATENT DOCUMENTS

| KR | 101138354 B1 | 4/2012 |
| WO | 9917716 A2 | 4/1999 |
| WO | 2016142323 A1 | 9/2016 |
| WO | 2018210602 A1 | 11/2018 |
| WO | 2019195694 A1 | 10/2019 |

OTHER PUBLICATIONS

Glass Ionomer Cement Formulations: I. The Preparation of Novel Fluoroaluminosilicate Glasses High in Fluorine; Journal of Dental Research; Jun. 1979; pp. 1607-1619.
International Search Report; PCT/EP2019/082753; Jan. 22, 2020 (completed); Jan. 31, 2020 (mailed).
Written Opinion of the International Searching Authority; PCT/EP2019/082753; Jan. 22, 2020 (completed); Jan. 31, 2020 (mailed).
International Preliminary Report on Patentability; PCT/EP2019/082753; Jan. 22, 2020 (completed); Jan. 31, 2020 (mailed).

\* cited by examiner

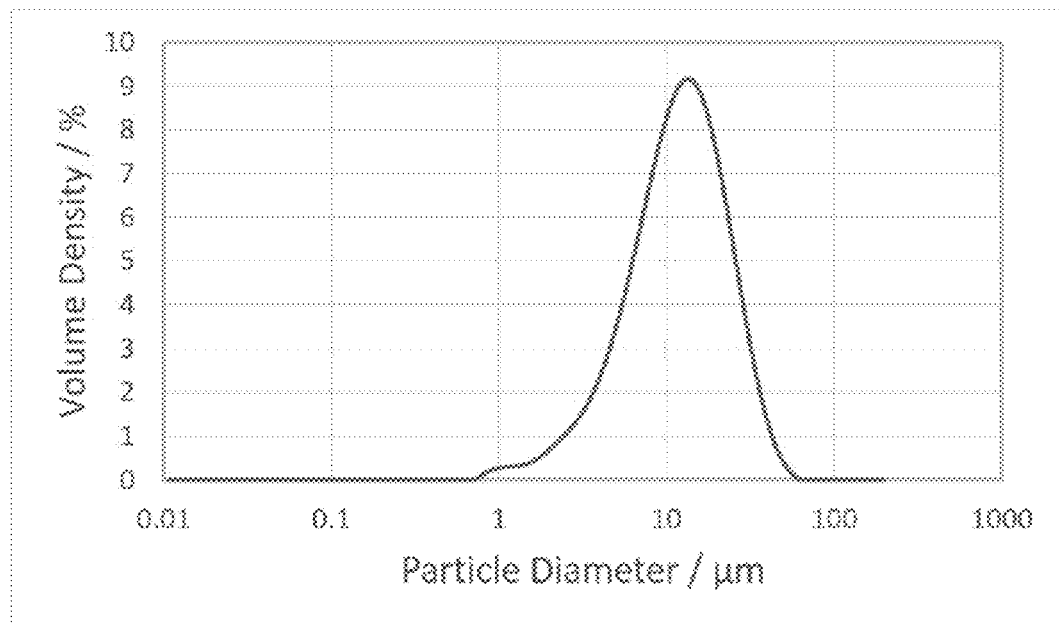

ADDITIVE MANUFACTURING PROCESS

FIELD OF THE INVENTION

The present invention relates to an additive manufacturing process. Moreover, the present invention relates to a cartridge for a 3D printer, and a kit-of-parts comprising a plurality of specific cartridges of the present invention. Finally, the present invention relates to a curable dental composition for use in the additive manufacturing process of the present invention.

The additive manufacturing process of the present invention may be used for the preparation of a wide range of solid objects. However, particular advantages are available in the rapid chairside or laboratory preparation of dental appliances having excellent dimensional accuracy, aesthetic and mechanical properties and which avoids extensive manual finishing.

BACKGROUND OF THE INVENTION

Dental appliances such as restorations are conventionally manufactured by subtractive milling and grinding processes using milling and grinding machines controlled by a software for machining a composite or ceramic block in a short period of time. According to a conventional subtractive process, an optical scan of the dentition of a patient is registered, analyzed and a dental model is designed by using a computer. The design is used for milling/grinding a solid block in about 4 to 12 minutes to a model with a precision of about 25 µm. The model may be subsequently sintered and finally glazed, which takes about 10 to 25 minutes. In addition, such ceramic restorations require surface treatment such as sand-blasting and/or chemical etching of the material surface to enhance the mechanical and/or chemical interaction with the cement used to adhere the restoration with the tooth substrate. Accordingly, the production of a dental appliance by a subtractive process may be carried out chairside in about 30 minutes.

However, computer-controlled milling and grinding machines are costly and require careful maintenance resulting in considerable maintenance costs. Additionally, most of the block material is lost in the subtractive milling and grinding process making the dental prosthesis cost high.

Additive manufacturing technologies using relatively low cost, small size, desktop 3D printer machines using biocompatible resin materials can be used for chairside fabrication of dental appliances such as restorative prostheses.

Additive manufacturing processes are conventionally used to create a physical object by layering materials one by one based on a digital model. For example, in Fused Filament Fabrication or Fused Deposition Modeling a thermoplastic material is processed in filament form to create three dimensional objects by extrusion of the plasticized material through a moving, heated printer extruder head. Molten material is forced out of the print head's nozzle and is deposited on the growing workpiece. The force required to extrude the melt must be sufficient to overcome the pressure drop across the system, which depends on the viscous properties of the melted material and the flow geometry of the liquefier and nozzle. Typical materials used for Fused Filament Fabrication are thermoplastic polymers such as acrylonitrile butadiene styrene (ABS) polymer, polylactic acid (PLA), glycol modified polyethylene terephthalate (PETG), nylon, and the like.

However, for the purpose of many dental applications, the mechanical properties or chemical resistance of the solidified thermoplastic materials are not acceptable.

Further common methods for additive manufacturing are based on layer-by-layer photocuring of low viscosity resin formulations supplied in a tray. Typical examples are SLA (stereolithography) or DLP (digital light processing). While such methods allow for high-speed and affordable 3D-printing, their demand for low viscosity resins (typically <6 Pas) limits suitable materials to low filler contents (<1%). Consequently, the printed physical objects deliver insufficient mechanical properties (flexural strength/E-modulus), limiting their application, to non-permanent restorations, surgical guides or splints. Moreover, SLA or DLP require extensive manual finishing such as excess resin removal using organic solvents, removal of support structures, as well as finishing and polishing.

Therefore, conventional 3D printing processes cannot be used chairside for the preparation of single unit permanent dental restorations such as crowns, inlays, onlays and veneers.

A material which is acceptable for the preparation of a single unit permanent dental restoration is a composite material comprising polymerizable resins, at least 50% by weight based on the total weight of the composition of particulate filler and a polymerization initiator system. The material is polymerized and forms a crosslinked polymer phase wherein the particulate filler is incorporated.

However, the use of a composite material in an extrusion or jetting step during additive manufacturing is problematic due to particle induced clogging of the fine nozzles required for high resolution printing.

WO 2016/142323 discloses a cartridge for a 3D printer. The cartridge has a nozzle or is designed in such a way that a predefined nozzle can be formed. The cartridge contains a dental composite material comprising a photocurable resin matrix and only fillers having a maximum particle diameter of less than 5 µm in order to avoid the clogging of a nozzle. For allowing extrusion through the nozzle, WO 2016/142323 teaches that the curable dental composite material preferably has a low viscosity in the range of 50 to 800 Pas. Therefore, the cohesive strength or consistency of the uncured composite material of WO 2016/142323 is low, and layers may tend to flow. Accordingly, each layer has to be cured before a subsequent layer may be printed. Moreover, a support material is required which must be removed after curing of the dental composite.

Accordingly, although the mechanical properties of a dental appliance are improved by the use of a composite material over conventional thermoplastic polymers, the dimensional accuracy, the production rate and mechanical properties of the process according to WO2016/142323 cannot compete with the dimensional accuracy, the production rate and mechanical properties of conventional subtractive processes. Even in the preparation of small dental appliances, the limited strength of the uncured material, the limited cohesive strength of the cured material and the required manual finishing prevent the process of WO2016/142323 from being useful for single unit permanent dental restorations such as crowns, inlays, onlays and veneers.

SUMMARY OF THE INVENTION

It is a problem of the present invention to provide an additive manufacturing process which may be used for the rapid chairside or laboratory preparation of dental appliances having excellent dimensional accuracy, aesthetic and mechanical properties and which avoid extensive manual finishing or surface treatment as required for dental restoratives produced by subtractive manufacturing or WO2016/142323.

The present invention provides an additive manufacturing process comprising:

(a) providing a curable composition comprising:
  (i) a filler comprising glassflakes having a diameter $D_{3,99}$ as determined by light scattering in the range of from 5 to 150 µm; and
  (ii) one or more curable compounds;
(b) controlling an apparatus to form an object by using the curable composition, whereby the curable composition passes a discharge orifice having a minimum diameter $\Phi_{min}$, wherein the ratio of the minimum diameter of the discharge orifice to the diameter $D_{3,99}$ of the glassflakes ($\Phi_{min}/D_{3,99}$) is in the range of 2 to less than 10.

Moreover, the present invention provides a cartridge for a 3D printer, which contains a curable dental composition, the cartridge having a discharge orifice for ejecting or extruding the curable composition during 3D printing wherein the ratio of the minimum diameter of the discharge orifice $\Phi_{min}$ to the diameter $D_{3,99}$ of the glassflakes as determined by light scattering ($\Phi_{min}/D_{3,99}$) is less than 10.

The present invention also provides a kit-of-parts comprising a plurality of cartridges of the invention, each cartridge containing a dental composition and optionally a support material, whereby the cartridge is marked to distinguish the dental composition from a support material or to identify a property of the cured dental composition, which property is preferably selected from the color, and/or opacity.

Finally, the present invention provides a specific curable composition comprising a photoinitiator.

The present invention is based on the recognition that a specific curable composition comprising a filler comprising glassflakes having a diameter $D_{3,99}$ as determined by light scattering in the range of from 5 to 150 µm, and one or more curable compounds has a low viscosity under shear stress as occurring during extrusion or jetting in an additive manufacturing process when the composite composition moves through a narrow discharge orifice. Accordingly, it is possible to increase the printing rate of the curable composition. Moreover, the specific curable composition has a high cohesive strength or slump resistance in an uncured state so that uncured structures of the curable composition do not have a tendency to flow, multiple layers may be printed before curing, and additional support structures may often be omitted. Therefore, the printing rate may be increased without impairing the resolution of the print and/or dimensional accuracy. Finally, the cured composite composition containing large glassflakes having a diameter $D_{3,99}$ as determined by light scattering in the range of from 5 to 150 µm provides excellent mechanical properties including flexural strength. Accordingly, the additive manufacturing process of the present invention may be used for the rapid chairside or laboratory preparation of dental appliances including single unit permanent dental restorations such as crowns, inlays, onlays and veneers, having excellent aesthetic and mechanical properties. Since extensive manual finishing may be avoided, the dimensional accuracy of the printed object is improved.

Surprisingly, the use of specific large glassflakes in a curable composition in combination with a shear stress inducing discharge orifice reducing the dynamic viscosity of the curable composition, does not lead to the dogging of the discharge orifice contrary to the dogging of a nozzle observed by large spherical filler particles as described in WO2016/142323.

BRIEF DESCRIPTION OF THE FIGURE

FIG. 1 shows the particle size distribution of GF350 nmM glassflakes after milling, wherein $D_{3,50}$=12.1 µm, $D_{3,99}$=42.5 µm.

DETAILED DESCRIPTION OF THE PREFERRED EMBODIMENTS

The term "additive manufacturing process" means herein any of various processes in which a composite composition is joined and cured under computer control to create a three-dimensional object. According to the present invention, the composite composition passes a discharge orifice having a minimum diameter $\Phi_{min}$. An additive manufacturing process according to the present invention may comprise material extrusion or material jetting. Material extrusion means that a material is drawn through a nozzle and is then deposited layer by layer. Material jetting is similar to inkjet document printing, but instead of jetting drops of ink onto paper, 3D printers jet drops of curable compositions onto the build tray.

The term "glassflake" as used herein means that a glass particle is in the form of small, flat, thin piece, typically one which has broken away from a larger piece of a glassflake, whereby its median diameter is larger than its thickness, preferably at least by a factor of 10. The ratio of median particle diameter ($D_{3,50}$) to average thickness is referred to as "average aspect ratio" herein.

The term "diameter $D_{3,99}$" or "$D_{3,99}$" as used herein in connection with the structural filler or the glassflakes refers to the diameter at which 99% of the sample's volume is comprised of particles with a diameter less than this value. The diameter $D_{3,99}$ is determined by a light scattering method. Accordingly, the parameter $D_{3,99}$ is computed for a particle diameter distribution determined by a light scattering method by modelling all particles as spheres. Several different attributes can be chosen to determine the diameter of an "equivalent sphere". According to the present invention, particles are modelled as spheres of equivalent volume. The $D_{3,99}$-value can be thought of as a "volume division diameter". $D_{3,99}$ is the diameter which, when all particles in a sample are arranged in order of ascending volume, divides the sample's volume into specified percentages. The percentage volume below the diameter of interest is the number expressed after the "$D_3$". Accordingly, the $D_{3,99}$ diameter is the diameter at which 99% of a sample's volume is comprised of smaller particles.

The term "median particle diameter" or $D_{3,93}$ as used herein in connection with the structural filler or the glassflakes refers to the diameter at which 50% of the sample's volume is comprised of particles with a diameter less than this value. The median particle diameter $D_{3,50}$ may be determined by any suitable means, such as light scattering or high-resolution scanning electron microscopy, preferably light scattering.

The term "particle size distribution" defines the relative amount by volume of particles present according to diameter.

The "average thickness" of the glassflakes as used herein may be determined as follows: The thicknesses of 200 or more glassflakes of a sample are determined by scanning electron microscopy (SEM). Then, the total sum of the measured thicknesses is divided by the number of glassflakes for which the thickness was determined.

The term "structural filler" as used herein means any dental filler other than the glassflakes or the further filler described below. Preferably, the structural filler is a dental glass, most preferably a dental glass selected from inert glasses, reactive glasses and fluoride releasing glasses.

The term "inert glass(es)" refers to a glass which is not capable of reacting with a polymer containing acidic groups in a cement reaction. Inert glasses are for example described in the Journal of Dental Research June 1979, pages 1607-1619, or more recently in U.S. Pat. Nos. 4,814,362, 5,318,929, 5,360,770, and application US 2004/0079258 A1. Specifically, from US 2004/0079258 A1, inert glasses are known in which strongly basic oxides such as CaO, BaO, SrO, MgO, ZnO, $Na_2O$, $K_2O$, $Li_2O$ etc. are replaced with weakly basic oxides such as those in the Scandium or Lanthanide series.

The term "sphericity" as used herein means the ratio of the surface area of a sphere with the same volume as the given particle in the form of structural filler to the surface area of the particle in the form of a structural filler. A spherical particle may have a sphericity of >80 percent.

The term "silanated" as used herein means that the glassflakes and/or the structural filler and/or any further filler such as a nanofiller have a surface provided with silane coupling agent(s), for example, in the form of a coating at least partially and preferably fully covering the surface. The "silane coupling agent" may be any organosilane having one or more polymerizable groups and one or more hydolyzable groups, such as (meth)acryl or vinyl, for example 3-methacryloyloxy trimethoxysilane, vinyltrichlorosilane, tris (2-methoxyethoxy)-vinylsilane or tris (acetoxy)-vinylsilane.

The terms "polymerization", "polymerizable", "curable" and "curing" relate to the combining or the capability to combine by covalent bonding of a large number of compounds such as smaller molecules, for example monomers, to form larger molecules, that is, macromolecules or polymers. The polymerizable compounds may be combined to form only linear macromolecules or they may be combined to form three-dimensional macromolecules, commonly referred to as crosslinked polymers. For example, monofunctional polymerizable compounds form linear polymers, whereas polymerizable compounds having at least two functional groups form crosslinked polymers also known as polymer networks.

The term "curable compounds" as used herein encompasses monomers, oligomers and polymers. Preferably, one or more curable compounds is/are monomers.

The terms "curing" and "photocuring" mean the polymerization of functional polymerizable compounds such as monomers, oligomers or even polymers, into a crosslinked polymer network. Curing is the polymerization of unsaturated polymerizable compounds in the presence of crosslinking agents.

"Actinic radiation" is any electromagnetic radiation that is capable of producing photochemical action and can have a wavelength of at least 150 nm and up to and including 1250 nm, and typically at least 300 nm and up to and including 750 nm.

The term "photoinitiator" is any chemical compound that forms free radicals when activated, e.g. by exposure to light or interaction with a coinitiator in a photochemical process.

The term "coinitiator" refers to a molecule that produces a chemical change in another molecule such as a photoinitiator in a photochemical process. The coinitiator may be a photoinitiator or an electron donor.

The term "electron donor" as used herein means a compound which is capable of donating electrons in a photochemical process. Suitable examples include organic compounds having heteroatoms with electron lone pairs, for example amine compounds.

The term "thermoinitiator" refers to a molecule that forms free radicals when activated, e.g. by exposure to heat above a defined threshold temperature.

The term "redox initiator" defines an initiator system comprises reducing and oxidizing agents, which produce free-radicals capable of initiating polymerization of the polymerizable group(s).

The Curable Composition

The additive manufacturing process of the present invention comprises a step of providing a curable composition. The curable composition comprises a filler. Preferably, the curable composition contains filler in an amount of greater than 1 to 85 percent by weight, more preferably 10 to 80 percent by weight, still more preferably 20 to 75 percent, based on the total weight of the composition. The filler may consist of glassflakes only. Preferably, the filler consists of glassflakes and one or more structural fillers.

The glassflakes have a diameter $D_{3,99}$ as determined by light scattering in the range of from 5 to 150 µm. Preferably, the diameter $D_{3,99}$ as determined by light scattering in the range of from 8 to 100 µm, more preferably 10 to 60 µm.

The curable composition may contain the glassflakes in an amount of from 0.5 to 83 percent by weight based on the total weight of the composition. Preferably, the curable composition contains glassflakes in an amount of 5 to 40 percent by weight, more preferably 10 to 25 percent by weight, based on the total weight of the composition Preferably, the glassflakes have a diameter $D_{3,93}$ of 3 to 25 µm, more preferably of 3 to 15 µm.

According to the present invention, the $D_{3,99}$ or $D_{3,50}$ are determined by using a light scattering method.

The glassflakes may have an average thickness between 50 nm and 1000 nm, preferably between 60 nm and 700 nm, more preferably between 70 nm and 600 nm, and most preferably between 80 nm and 500 nm.

The glassflakes may have an average aspect ratio (median particle diameter ($D_{3,50}$)/average thickness) in the range of from 2:1 to 50:1, more preferably at least 10:1.

The glass of the silanated glassflakes is preferably an inert glass. The glass of the glassflakes preferably comprises the following components as oxides in percent by weight:

$SiO_2$=64-70
$B_2O_3$=2-5
ZnO=1-5
$Na_2O$=8-13
MgO=1-4
CaO=3-7
$Al_2O_3$=3-6, and up to 3 percent of $K_2O$ and $TiO_2$.

The glassflakes are preferably obtainable by milling glassflakes having an aspect ratio of at least 20:1, and subsequently silanating the milled glassflakes. The milling of the glassflakes is not particularly limited and may be carried out with any apparatus typically applied for milling dental filler materials, such as a ball milling apparatus, or a pearl mill apparatus.

The particle diameter of the milled glassflakes may, for example, be suitably set by milling conditions selected from median particle diameter of the glassflakes used as starting material, grinding time, as well as amount, size and material of the grinding material such as balls or pearls and fluid such as water.

For example, for milling, as a starting material, glassflakes may be used which have a median particle diameter determined by light scattering of less than 700 μm, more preferably 40 to 500 μm, and most preferably 50 to 300 μm.

When adding unwashed glassflakes into a dental composition, often greyish pastes are obtained. For better aesthetical results, the glassflakes may be washed prior to coating. For washing, the glassflakes may be stirred in an excess amount of dilute acid such as hydrochloric acid, preferably for 1 minute to 24 hours, advantageously for half an hour, and then filtered off and washed with about the twentyfold amount of water during filtration. Finally, the glassflakes may be dried at a temperature of from ambient temperature to 200° C., preferably 50° C. to 100° C. for 1 minute to 48 hours.

By setting the particle size distribution of the milled glassflakes prior to silanation, the extrusion force for extruding the uncured dental composition according to the invention through a nozzle can be advantageously set within the desired range. In addition, the cured dental composition has advantageous mechanical properties such as a flexural strength of up to 150 MPa, typically about 100 to 140 MPa, and E-modulus of up to 10 GPa, typically about 5 to 8 GPa.

The thus obtained milled glassflakes may be silanated with a silane having one or more polymerizable groups reactive with the polymerizable compounds. Silanes for silanating filler materials of dental compositions are well known and a large variety thereof for dental applications is described for example by J. M. Antonucci, Journal of Research of the National Institute of Standards and Technology, 2005, vol. 110, no. 5, pages 541 to 558. Preferably, during silanation, the suspension may be treated with ultrasound.

Typically, organosilanes of formula (I)

$(R_1,R_2,R_3)Si(R_H)_n$          (I)

are applied, wherein n is 1 to 3 and the number of substituents $R_1$, $R_2$, $R_3$ is 4 n, wherein at least one of $R_1$, $R_2$, $R_3$ represents a polymerizable group. $R_H$, which may be the same or different if two or three groups $R_H$ are present, represent(s) a hydrolysable group capable of reacting with the surface of the, filler material to be coated. $R_H$ may be selected from the group consisting of alkoxy groups, ester groups, halogen atoms and amino group, wherein the alkoxy groups are preferably linear $C_{1-8}$ or branched or cyclic $C_{3-8}$ alkoxy groups, and the ester groups are preferably carboxylates having linear $C_{1-8}$ or branched or cyclic $C_{3-8}$ alkyl groups. Most preferably, the hydrolysable group $R_H$ represents an alkoxy group.

The groups $R_1$, $R_2$ and $R_3$ may be the same or different and represent unreactive groups and/or polymerizable groups, with the proviso that at least one of $R_1$, $R_2$ and $R_3$ represents a polymerizable group. Unreactive groups for $R_1$, $R_2$ and $R_3$ may be represented by alkyl groups, preferably linear $C_{1-8}$ or branched or cyclic $C_{3-8}$ alkyl groups. Polymerizable groups for $R_1$, $R_2$ and $R_3$ are preferably selected from the group consisting of a (meth)acryl group, a vinyl group or an oxirane group, more preferably (meth)acryl group or a vinyl group, and most preferably a (meth)acryl group which may be in the form of e.g. methacryloxy or methacryloxyalkyl wherein alkyl means a linear $C_{1-8}$ or branched or cyclic $C_{3-8}$ alkyl group.

Particularly preferred organosilanes are for example 3-methacryloxy trimethoxysilane, vinyltrichlorosilane, tris (2-methoxyethoxy)-vinylsilane or tris(acetoxy)-vinylsilane, or any one of the specific group of organosilanes disclosed in EP 0969789 A1, namely 3-methacryloxypropyltrimethoxysilane, 3-methacryloxypropyldimethoxy-monochlorosilane, 3-methacryloxypropyldichloromonomethoxysilane, methacryloxypropyltri-chlorosilane, 3-methacryloxypropyl-dichloromonomethyl-silane, 3-methacryloxypropylmono-chlorodimethylsilane and 3-(trimethoxysilyl)propyl methacrylate.

Most preferably, the organosilane of formula (I) is 3-(trimethoxysilyl)propyl methacrylate.

Alternatively or additionally to the organosilanes of formula (I), so-called dipodal organosilanes may be applied. Dipodal organosilanes are typically compounds of formula (II)

$((R_H)_3Si-R_4)_2CH-R_1$          (II), wherein $R_1$ and $R_H$ have the same meaning as defined above for the organosilane of formula (I), and $R_4$ represents an alkylene group, preferably a linear $C_{1-8}$ or branched or cyclic $C_{3-8}$ alkylene group.

According to the present invention, the filler of the curable composition may further comprise a structural filler so that the curable composition comprises a combination of glassflakes and structural filler. The combination of glassflakes and structural filler is useful for adjusting the viscosity of the curable composition within a desired range and for adjusting the mechanical properties of the cured composition. The combination of the glassflakes and the structural filler is specifically selected in order to attain well balanced properties for the cured dental composition. Owing to the specific combination of silanated glassflakes and the structural filler, excellent gloss, gloss retention and long-term chemical and abrasion resistance may be attained as well as excellent mechanical properties and long-term mechanical resistance.

According to a preferred embodiment, the structural filler has a $D_{3,99}$ particle diameter of less than 5 μm.

Preferably, the structural filler has a median particle diameter $D_{3,50}$ of from 0.3 to 2 μm, more preferably of from 0.4 to 1.2 μm.

Preferably, the curable composition has an extrusion force of below 100 N at room temperature (23° C.), when extruding the uncured composition through a nozzle having a diameter of 600 μm and a length of 11 mm. Furthermore, the cured composition has advantageous mechanical properties such as a flexural strength of at least about 100 MPa, preferably 100 to 140 MPa, and an E-modulus of at least 5 GPa, preferably 5 to 8 GPa. As a result, the curable composition can be easily extruded or jetted, and the cured composition exhibits excellent mechanical properties.

Preferably, the structural filler has a median particle diameter $D_{3,50}$ of from 0.4 to 1.2 μm, and the silanated glassflakes have (a) an average thickness between 50 nm and 1000 nm, and (b) an average aspect ratio (median particle diameter/average thickness) in the range of from 10:1 to 50:1.

Preferably, the dental composition contains the glassflakes in an amount of from 0.5 to 40 percent, more preferably 1 to 30 percent, even more preferably 10 to 25, or 3 to 20 percent by weight based on the total weight of the composition.

In the curable composition, the ratio of the weight of structural filler and the weight of the glassflakes is preferably in the range of from 80:1 to 1:80, more preferably 40:1 to 1:1, even more preferably 20:1 to 1.5:1, yet even more preferably 10:1 to 2:1 and most preferably 5:1 to 2.5:1.

According to an alternative, particular preferred embodiment, in the dental composition, a ratio of the weight of the glassflakes to the weight of structural filler is preferably 0.025:1 to 2:1, more preferably 0.05:1 to 1.5:1, even more preferably 0.075:1 to 1:1, yet even more preferably 0.1:1 to 0.75:1 and most preferably 0.125:1 to 0.6:1.

Preferably the refractive index of the glassflakes and the structural filler is in the range of 1.40 to 1.60, respectively.

The curable composition further comprises one or more curable compounds. The curable compounds have at least one polymerizable group.

The polymerizable group of the one or more curable compounds is not particularly limited. At least one polymerizable group may for example be a radically polymerizable carbon-carbon double bond and/or a cationically polymerizable group. Preferably, radically polymerizable carbon-carbon double bonds are selected from carbon-carbon double bonds of (meth)acryloyl group(s) and a (meth)acrylamide group, preferably (meth)acryloyl group(s). Further, it is preferred that the cationically polymerizable groups are selected from epoxide groups, oxetane groups, vinyl ether groups, aziridine groups, and azetidine groups, preferably from epoxide groups, vinyl ether groups and oxetane groups, most preferably from epoxide groups and vinyl ether groups.

One or more curable compounds having at least one radically polymerizable carbon-carbon double bonds are not particularly limited. However, preferably, their radically polymerizable carbon-carbon double bonds are selected from carbon-carbon double bonds of a (meth)acryloyl group and a (meth)acrylamide group.

Suitable examples of polymerizable compounds having at least one radically polymerizable carbon-carbon double bonds may be selected from the group consisting of (meth)acrylates, amides of acrylic or methacrylic acid, urethane acrylates or methacrylates, and polyol acrylates or methacrylates.

(Meth)acrylates may be preferably selected from compounds of the following formulae (A), (B) and (C):

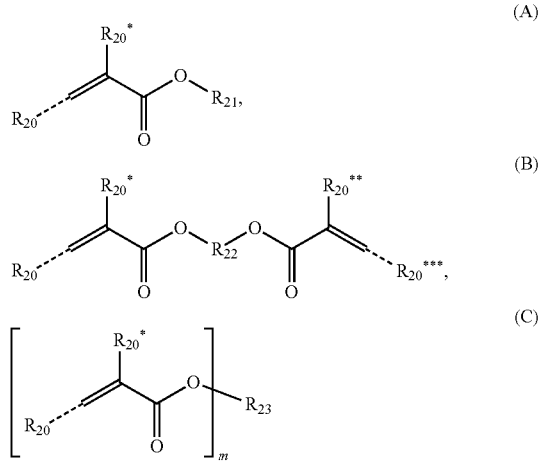

wherein $R_{20}$, $R^*_{20}$, $R^{}_{20}$, and $R^{*}_{20}$ independently represent a hydrogen atom, a linear $C_{1-18}$ or branched $C_{3-18}$ alkyl group which may be substituted by a $C_{3-6}$ cycloalkyl group, a $C_{6-14}$ aryl or $C_{3-14}$ heteroaryl group, a $C_3$ to $C_{18}$ cycloalkyl group which may be substituted by a $C_{1-16}$ alkyl group, a $C_{6-14}$ aryl or $C_{3-14}$ heteroaryl group, or a $C_5$ to $C_{18}$ aryl or $C_3$ to $C_{18}$ heteroaryl group, $R_{21}$ represents a hydrogen atom, a linear $C_{1-18}$ or branched $C_{3-18}$ alkyl group or $C_2$ to $C_{18}$ alkenyl group which may be substituted by a $C_{3-6}$ cycloalkyl group, a $C_{6-14}$ aryl or $C_{3-14}$ heteroaryl group, a $C_3$ to $C_{18}$ cycloalkyl group which may be substituted by a $C_{1-16}$ alkyl group, a $C_{6-14}$ aryl or $C_{3-14}$ heteroaryl group, or a $C_5$ to $C_{18}$ aryl or $C_3$ to $C_{18}$ heteroaryl group, $R_{22}$ represents a divalent organic residue having from 1 to 45 carbon atoms, whereby the divalent organic residue may contain at least one of from 1 to 7 $C_{3-12}$ cycloalkylene group(s), 1 to 7 $C_{6-14}$ arylene groups, 1 to 7 carbonyl groups, 1 to 7 carboxyl groups (—(C═O)—O— or —O—(C═O)—), 1 to 7 amide groups (—(C═O)—NH— or NH—(C═O)—) or 1 to 7 urethane groups (—NH—(C═O)—O— or O—(C═O)—NH—), and 1 to 14 heteroatoms selected from oxygen, nitrogen and sulphur, which divalent organic residue may be substituted with one or more substituents selected from the group consisting of a hydroxyl group, a thiol group, a $C_{6-14}$ aryl group; preferably Rn is a $C_1$ to $C_{18}$ alkylene group or a $C_2$ to $C_{18}$ alkenylene group, which may be substituted by one or more OH group(s), which alkylene or alkenylene group may contain at least one of 1 to 4 $C_{6-10}$ arylene groups, 1 to 4 urethane groups (—NH—(C═O)—O— or O—(C═O)—NH—), and 1 to 8 oxygen atoms;

$R_{23}$ represents a saturated di- or multivalent substituted or unsubstituted $C_2$ to $C_{18}$ hydrocarbon group, a saturated di- or multivalent substituted or unsubstituted cyclic $C_3$ to $C_{18}$ hydrocarbon group, a di- or multivalent substituted or unsubstituted $C_4$ to $C_{18}$ aryl or heteroaryl group, a di- or multivalent substituted or unsubstituted $C_5$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen atoms, and m is an integer, preferably in the range from 1 to 10.

For $R_{20}$, $R^*_{20}$, $R^{}_{20}$ and $R^{*}_{20}$, the linear $C_{1-18}$ or branched $C_{3-18}$ alkyl group may e.g. be methyl, ethyl, n-propyl, i-propyl, n-butyl, isobutyl, tert-butyl, sec-butyl, pentyl or hexyl. For $R_{21}$ and $R^*_{21}$, the $C_{1-18}$ alkyl group or $C_{2-18}$ alkenyl group may e.g. be eth(en)yl, n-prop(en)yl, i-prop(en)yl, n-but(en)yl, isobut(en)yl, tert-but(en)yl sec-but(en)yl, pent(en)yl or hex(en)yl.

For $R_{20}$, $R^*_{20}$, $R^{}_{20}$, $R^{*}_{20}$ and $R_{21}$ an aryl group may, for example, be a phenyl group or a naphthyl group, and a $C_{3-14}$ heteroaryl group may contain 1 to 3 heteroatoms selected from nitrogen, oxygen and sulfur.

For $R_{22}$, in the phrase "divalent organic residue may contain at least one of . . . " means that the groups which may be contained in the divalent organic residue are incorporated in the divalent organic residue by means of covalent bonding. For example, in BisGMA, two aryl groups in the form of phenyl and two heteroatoms in the form of oxygen are incorporated into the divalent organic residue of $R_{22}$. Or, as a further example, in UDMA, two urethane groups (—NH—(C═O)—O— or O—(C═O)—NH—) are incorporated in the divalent organic residue of $R_{22}$.

In formula (B), the dotted bond indicates that $R_{20}$ and $R^{***}20$ may be in (Z) or (E) configuration relative to CO.

Preferably, in formulae (A), (B) and (C), $R_{20}$, $R^*_{20}$, $R^{}_{20}$ and $R^{*}_{20}$ independently represent a hydrogen atom, a linear $C_{1-16}$ or branched $C_{3-16}$ alkyl group which may be substituted by a $C_{3-6}$ cycloalkyl group, a $C_{6-14}$ aryl or $C_{3-14}$ heteroaryl group, a $C_{3-6}$ cycloalkyl group which may be substituted by a $C_{1-16}$ alkyl group, a $C_{6-14}$ aryl or $C_{3-14}$ heteroaryl group, a $C_{6-14}$ aryl or $C_{3-14}$ heteroaryl group. More preferably, in formula (B), $R_{20}$, $R^*_{20}$, $R^{}_{20}$ and $R^{}_{20}$ independently represent a hydrogen atom, a linear $C_{1-8}$ or branched $C_{3-8}$ alkyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{20}$, $R^*_{20}$, $R^{}_{20}$ and $R^{*}_{20}$ independently represent a hydrogen atom, a linear $C_{1-4}$ or branched $C_3$ or $C_4$ alkyl group which may be substituted by a cyclohexyl group or a phenyl group, or a cyclohexyl group which may be substituted by a $C_{1-4}$ alkyl group. Most preferably, $R_{20}$, $R^*_{20}$, $R^{}_{20}$ and $R^{*}_{20}$ independently represent a hydrogen atom or a linear $C_{1-4}$ or branched $C_3$ or $C_4$ alkyl group.

Preferably, in formula (A), $R_{21}$ represents a hydrogen atom, a linear $C_{1-16}$ or branched $C_{3-16}$ alkyl group or $C_{2-16}$ alkenyl group which may be substituted by a $C_{3-6}$ cycloalkyl group, a $C_{6-14}$ aryl or $C_{3-14}$ heteroaryl group, a $C_{3-6}$ cycloalkyl group which may be substituted by a $C_{1-16}$ alkyl group, a $C_{6-14}$ aryl or $C_{3-14}$ heteroaryl group, a $C_{6-14}$ aryl or $C_{3-14}$ heteroaryl group. More preferably, $R_{21}$ represents a hydrogen atom, a linear $C_{1-10}$ or branched $C_{3-10}$ alkyl or $C_{2-10}$ alkenyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{21}$ represents is a hydrogen atom, a linear $C_{1-10}$ or branched $C_{3-10}$ alkyl group or linear $C_{2-10}$ or branched $C_{3-10}$ alkenyl group which may be substituted by a cyclohexyl group or a phenyl group, or a cyclohexyl group which may be substituted by a $C_{1-4}$ alkyl group. Yet even more preferably, $R_{21}$ represents an unsubstituted $C_{1-10}$ alkyl group or $C_{2-10}$ alkenyl group, still even more preferably an unsubstituted $C_{2-6}$ alkyl group or $C_{3-6}$ alkenyl group, and most preferably an ethyl group or an allyl group.

The (meth)acrylate compounds of formulae (A), (B) and (C) may be selected from the group consisting of methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, bisphenol A glycerolate dimethacrylat ("bis-GMA", CAS-No. 1565-94-2), 4,4,6,16 (or 4,6,6,16)-tetramethyl-10,15-dioxo-11,14-dioxa-2,9-diazaheptadec-16-enoicacid 2-[(2-methyl-1-oxo-2-propen-1-yl)oxy]ethyl ester (CAS no. 72869-86-4) JUDMA), glycerol mono- and di-acrylate such as 1,3-glycerol dimethacrylate (GDM), glycerol mono- and dimethacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxyethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethyihexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4 (2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acrylate]propane.

Most preferably, a compound of formula (B) is selected from the group consisting of:

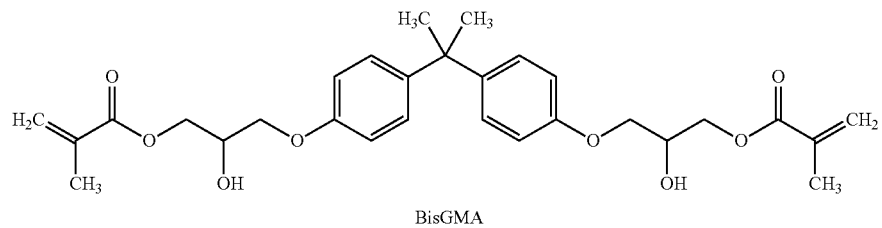

BisGMA

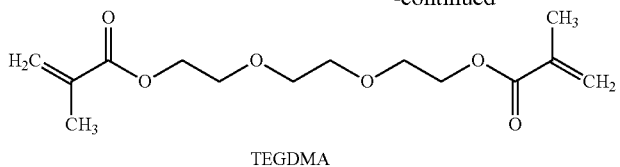

TEGDMA

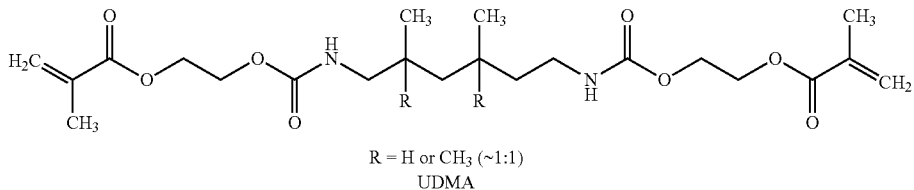

R = H or CH₃ (~1:1)
UDMA

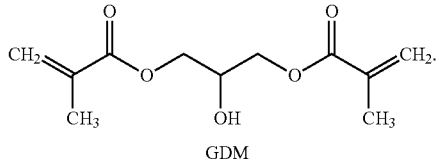

GDM

Particular preferred mono- or bis- or (meth)acrylamides and poly[(meth) acrylamides] have the following formulae (D), (E) and (F):

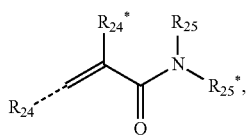 (D)

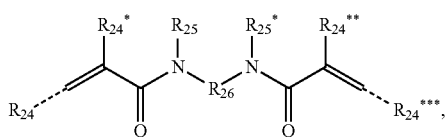 (E)

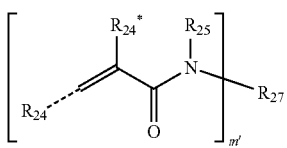 (F)

wherein $R_{24}$ $R^*_{24}$, $R^{}_{24}$, and $R^{*}_{24}$ have the same meaning as $R_{20}$ $R^*_{20}$, $R^{}_{20}$, $R^{*}_{21}$) defined above for formulae (A), (B) and (C), $R_{25}$, $R^*_{25}$ independently represent a residue having the same meaning as $R_{21}$ defined above for formula (A), and $R_{27}$ and m' have the same meaning as $R_{23}$ and m defined above for formula (C).

In formula (E), $R_{26}$ represents a divalent substituted or unsubstituted organic residue having from 1 to 45 carbon atoms, whereby said organic residue may contain at least one of 1 to 7 $C_{3-12}$ cycloalkylene group(s), 1 to 7 $C_{6-14}$ arylene groups, from 1 to 7 carbonyl groups, 1 to 7 carboxyl groups (—(C=O)—O— or —O—(C=O)—), 1 to 7 amide groups (—(C=O)—NH— or NH—(C=O)—), 1 to 7 urethane groups (—NH—(C=O)—O— or O—(C=O)—NH—), and 1 to 14 heteroatoms selected from oxygen, nitrogen and sulphur, which divalent organic residue may be substituted with one or more substituent(s) selected from the group consisting of a hydroxyl group, a thiol group, a $C_{6-14}$ aryl group, —COOM, —PO₃M, —O—PO₃M₂ or SO₃M*
Preferably, $R_{26}$ is a $C_1$ to $C_{18}$ alkylene group or a $C_2$ to $C_{18}$ alkenylene group which may contain at least one of 1 to 4 $C_{6-10}$ arylene groups and $C_{3-8}$ cycloalkylene group, 1 to 4 urethane groups (—NH—(C=O)—O— or O—(C=O)—NH—), and 1 to 8 oxygen atoms or nitrogen atoms.

For $R_{26}$, the phrase "divalent organic residue may contain at least one of . . . " has an analogous meaning as defined above for $R_{22}$ of compound of formula (B).

In formulae (D), (E), (F), the dotted bond indicates that $R_{24}$ and $R^{***}_{24}$ may be in (Z) or (E) configuration relative to CO.

In compound of formula (D), $R_{25}$ and $R_{25}^*$ may cooperatively form a ring in which $R_{25}$ and $R_{25}^*$ are linked by a C—C bond or a functional group selected from the group consisting of an ether group, a thioether group, an amine group and an amide group.

Preferred methacrylamides according to formulae (D), (E), (F) have the following formulae:

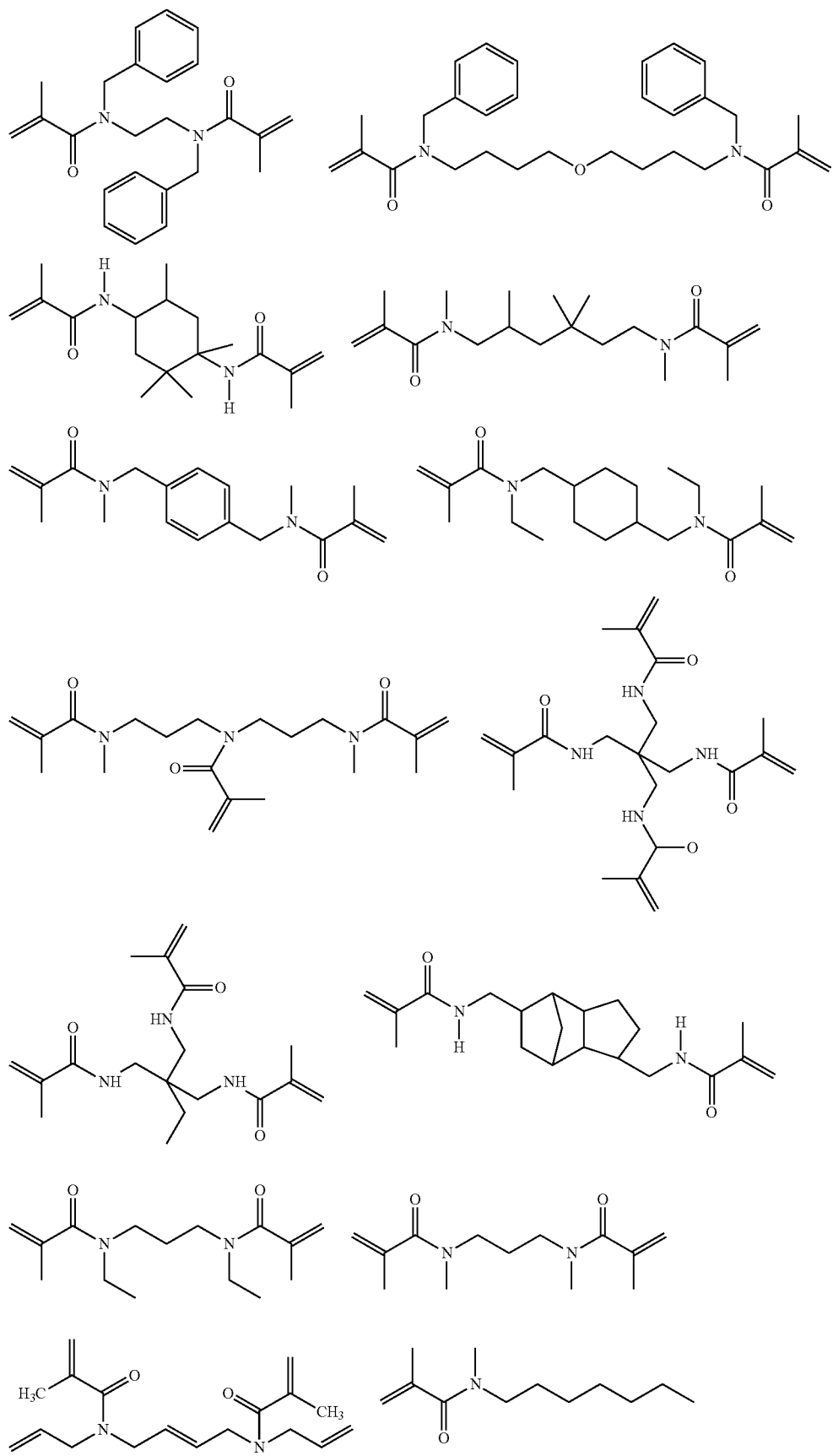

-continued
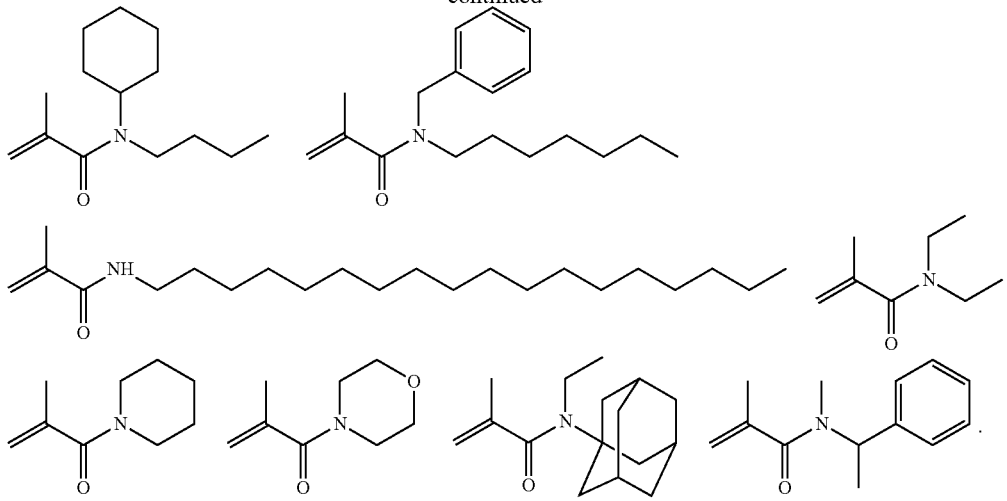
Preferred acrylamides according to formulae (D), (E), (F) have the following formulae:
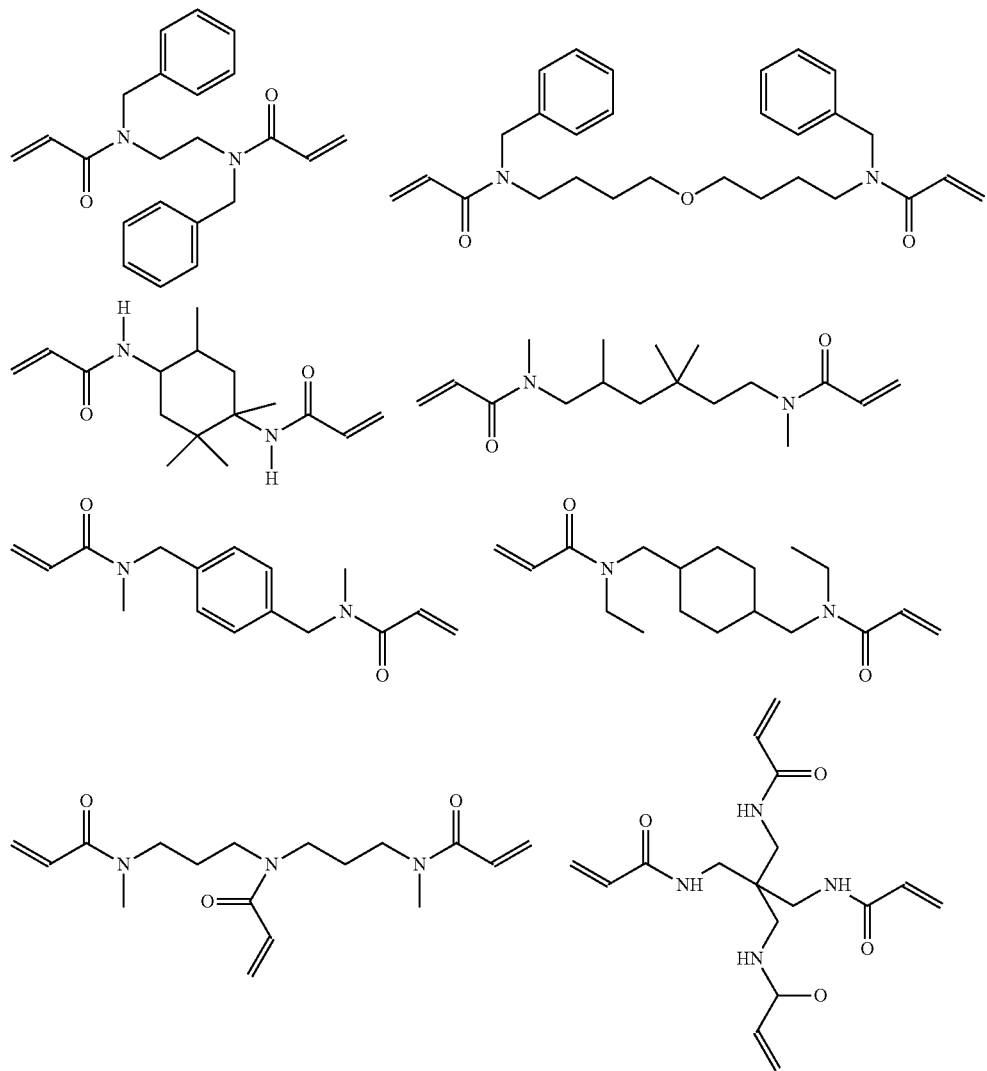

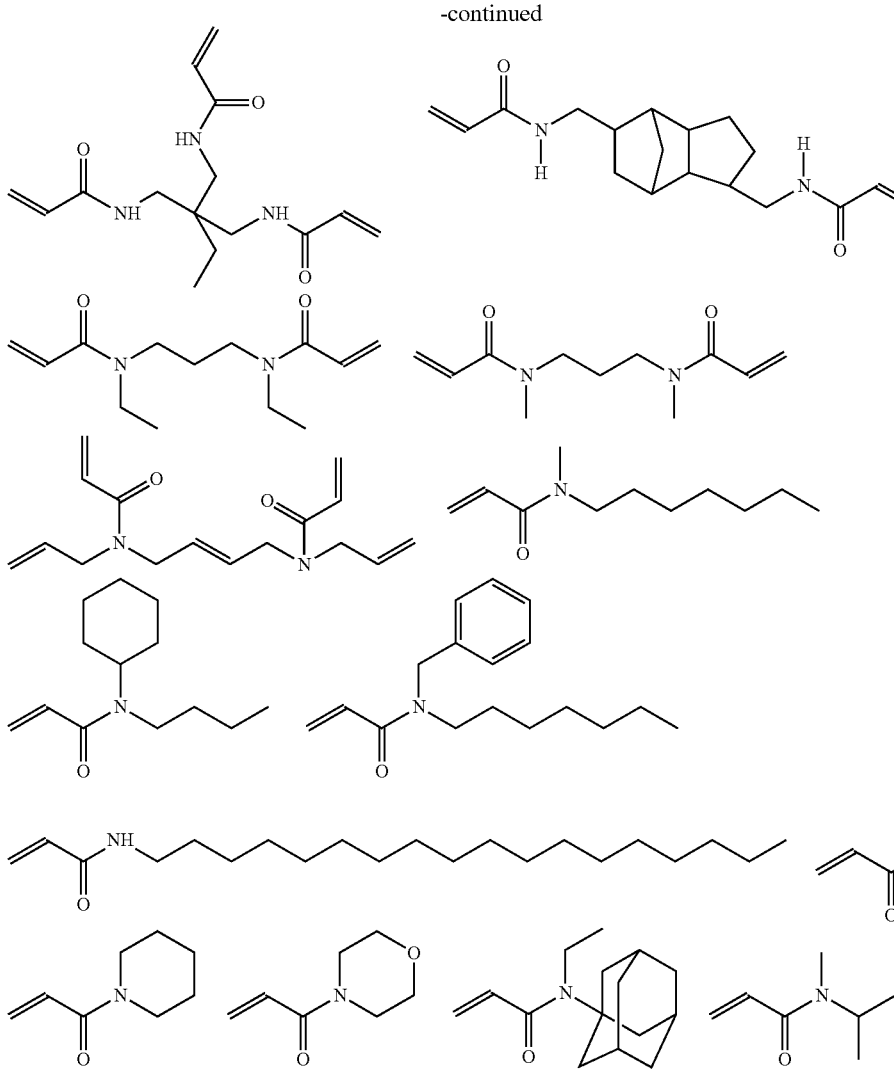

Most preferred are the bis-(meth)acrylamides:
N,N'-diallyl-1,4-bisacrylamido-(2E)-but-2-en (BAABE) having the structural formula

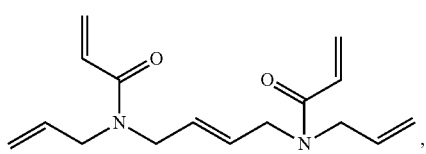 [SMILES: C=CCN(C/C=C/CN(CC=C)C(=O)C=C)C(=O)C=C]

and
N,N'-diethyl-1,3-bisacrylamido-propan (BADEP) having the structural formula

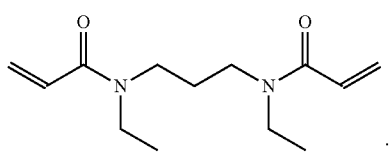 [SMILES: C=CC(=O)N(CC)CCCN(CC)C(=O)C=C]

Furthermore, compounds having one or more radically polymerizable carbon-carbon double bonds may be selected from the hydrolysis stable polyfunctional polymerizable monomers disclosed in EP 2 705 827 and EP 2 727 576.

Particularly preferred compounds having one or more radically polymerizable carbon-carbon double bonds are selected from the compounds of formulae (A), (B), (C), (G), (H), more preferably from the compound of formulae (A), (B), (C), and most preferably from compounds of formula (B).

The one or more curable compounds having one or more cationically polymerizable groups are not particularly limited. However, preferably, their cationically polymerizable groups are selected from epoxide groups, oxetane groups, vinyl ether groups, aziridine groups, and azetidine groups, more preferably from epoxide groups, oxetane groups and vinyl ether groups, and most preferably from epoxide groups and vinyl ether groups.

A compound having one or more cationically polymerizable groups in the form of an epoxide and/or oxetane group may be preferably selected from the compounds of the formulae (J), (K), (L):

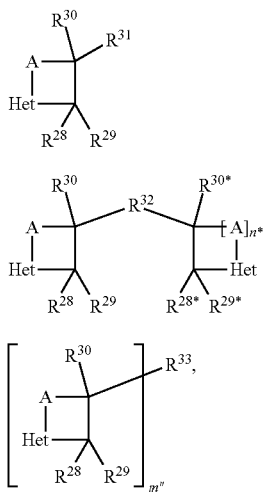

wherein

A is a single bond, a methylene (—CH$_2$—) group or a —R$^{28}$CR$^{28}$ in which R$^{28}$ and R$^{28}$ have the same meaning as defined below for R$^{28}$ and R$^{29}$, preferably A is a single bond or a methylene (—CH$_2$—) group, most preferably A is a single bond, Het is an oxygen atom or a nitrogen atom, preferably an oxygen atom, R$^{28}$, R$^{29}$, R$^{30}$, R$^{28*}$, R$^{29*}$, R$^{30*}$, R$^{31}$ independently represent a hydrogen atom, —COOM, or an organic moiety selected from the group consisting of a linear C$_{1-18}$ or branched or cyclic C$_{3-18}$ alkyl group which may be substituted by a C$_{3-6}$ cycloalkyl group, a C$_{6-14}$ aryl or C$_{3-14}$ heteroaryl group, a C$_3$ to C$_{18}$ cycloalkyl group which may be substituted by a linear C$_{1-16}$ or branched or cyclic C$_{3-16}$ alkyl group, a C$_{6-14}$ aryl or C$_{3-14}$ heteroaryl group, or a C$_5$ to C$_{18}$ aryl or C$_3$ to C$_{18}$ heteroaryl group, which organic moiety may be substituted with one or more substituent(s) selected from the group consisting of, R$^{32}$ represents a divalent organic residue having from 1 to 45 carbon atoms, whereby said organic residue may contain at least one of 1 to 7 C$_{3-12}$ cycloalkylene group(s), 1 to 7 C$_{6-14}$ arylene groups, 1 to 7 carbonyl groups, 1 to 7 carboxyl groups (—(C=O)—O— or —O—(C=O)—), 1 to 7 amide groups (—(C=O)—NH— or —NH—(C=O)—), 1 to 7 urethane groups (—NH—(C=O)—O— or —O—(C=O)—NH—), 1 to 14 heteroatoms selected from silicon, oxygen, nitrogen and sulphur; preferably R$^{32}$ is a C$_1$ to C$_{18}$ alkylene group which may contain at least one of 1 to 4 carboxyl groups (—(C=O)—O— or —O—(C=O)—)) or at least one moiety —SiR*$_2$—O—SiR*$_2$— wherein R* independently represent a linear C$_{1-4}$ or branched C$_3$ or C$_4$ alkyl group, which divalent organic residue may be substituted with one or more group selected from the group consisting of —OH, —SH;

and R$^{33}$ represents a saturated di- or multivalent substituted or unsubstituted linear C$_1$ to C$_{18}$ hydrocarbon group, a saturated di- or multivalent substituted or unsubstituted branched or cyclic C$_3$ to Ga hydrocarbon group, a di- or multivalent substituted or unsubstituted C$_6$ to C$_{18}$ aryl or heteroaryl group, a di- or multivalent substituted or unsubstituted C$_5$ to C$_{18}$ alkylaryl or alkylheteroaryl group, a di- or multivalent substituted or unsubstituted C$_7$ to C$_{30}$ aralkyl group, or a di- or multivalent substituted or unsubstituted C$_2$ to C$_{45}$ mono-, di-, or polyether residue having from 1 to 14 oxygen or sulphur atoms, and m* is an integer, preferably in the range from 1 to 10.

In compound of formulae (J), (K) and (L), R$^{28}$, R$^{30}$ and R$^{28*}$, R$^{30*}$ independently may cooperatively form a ring in which R$^{28}$, R$^{30}$ and R$^{28*}$, R$^{30*}$ are linked by a C—C bond or a functional group selected from the group consisting of an ether group, a thioether group, an amine group and an amide group. Preferably, R$^{28}$, R$^{30}$ and R$^{28*}$, R$^{30*}$ are linked by a C—C bond and form, together with the C—C bond located between R$^{28}$, R$^{30}$ and R$^{28*}$, R$^{38*}$ a 3 to 8 membered ring, preferably a 5 to 7 membered ring, most preferably a C$_6$ ring.

For R$^{32}$, the phrase "divalent organic residue may contain at least one of . . . " has an analogous meaning as defined above for R$_{22}$ of compound of formula (B).

It is preferred that in formula (J), Het is oxygen, R$^{28}$ and R$^{29}$ independently represent a linear C$_{1-8}$ or branched or cyclic C$_{3-8}$ alkyl group which may be substituted with one or more OH groups. More preferably, in formula (J), Het is oxygen, R$^{28}$ and R$^{29}$ independently represent a linear C$_{1-8}$ alkyl group which may be substituted with one or more OH groups, and R$^{30}$ and R$^{31}$ represent hydrogen atoms, wherein A is preferably a methylene (—CH$_2$—) group.

It is preferred that in formula (K), A is a single bond, Het is oxygen, R$^{28}$, R$^{30}$ and R$^{28*}$, R$^{30*}$ independently cooperatively form a ring in which R$^{29}$, R$^{30}$ and R$^{28*}$, R$^{30*}$ are linked by a C—C bond, and R$^{32}$ is a C$_1$ to C$_8$ alkylene group which may contain at least one of 1 to 4 carboxyl groups (—(C=O)—O— or —O—(C=O)—)) or at least one moiety SiR*$_2$—O—SiR*$_2$— wherein R independently represent a linear C$_{1-4}$ or branched C$_3$ or C$_4$ alkyl group.

Preferably, compounds of formulae (J) and (K) are selected from the group consisting of:

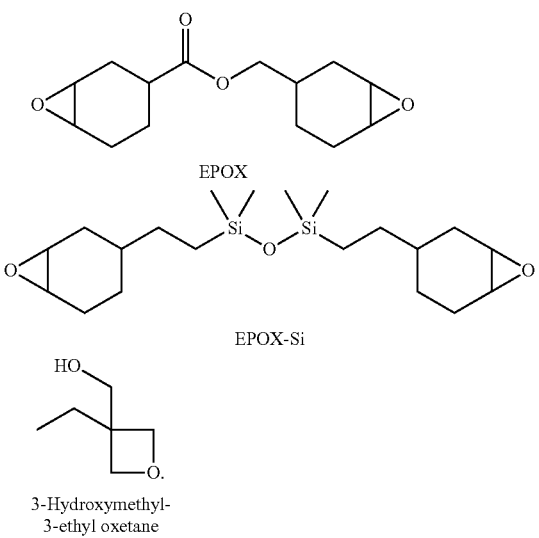

Most preferred are compounds of formula (K) being EPOX and/or EPOX-Si.

A compound having one or more cationically polymerizable groups in the form of a vinyl ether group may be preferably selected from the compounds of the formulae (M), (N), (O):

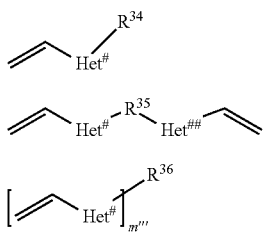

(M)
(N)
(O)

$R^{34}$ has the same meaning as $R^{21}$ defined above for formula (A) or may alternatively represent a monovalent substituted or unsubstituted $C_2$ to $C_{45}$ mono-, di-, or polyether residue having from 1 to 14 oxygen atoms, $R^{35}$ has the same meaning as $R^{22}$ defined above for formula (B), and $R^{36}$ and m''' have the same meaning as $R^{23}$ and m' as defined above for formula (C).

Preferably, in compound of formula (M), Het$^{\#}$ is an oxygen atom and $R^{34}$ represents a linear $C_{1-14}$ or branched or cyclic $C_{3-14}$ alkyl group, or an ethylenglycol moiety of formula $[-O-CH_2-CH_2-]_n-R^Y$ with n=1 to 9 and $R^Y$ being hydrogen or OH.

Preferably, in compound of formula (N), Het$^{\#}$ and Het$^{\#\#\#}$ are oxygen atoms and $R^{35}$ represents a $C_1$ to $C_{18}$ alkylene group which may contain at least one of 1 to 4 $C_{3-8}$ cycloalkylene group or 1 to 9 oxygen atoms, wherein the oxygen atoms may be contained such that an ethylenglycol moiety of formula $[-O-CH_2-CH_2-]_n-$ with n=1 to 9 is formed.

Most preferably, compounds of formulae (M) and (N) are selected from the group consisting of:

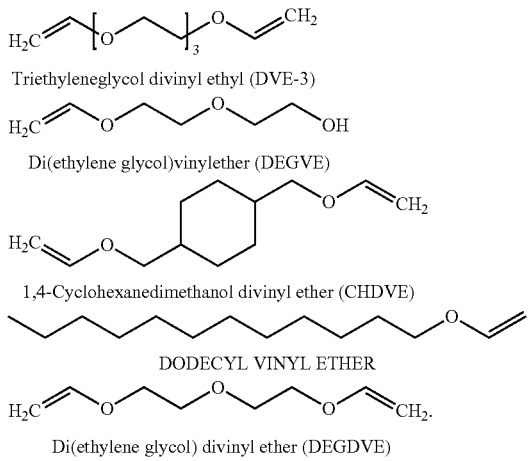

Triethyleneglycol divinyl ethyl (DVE-3)

Di(ethylene glycol)vinylether (DEGVE)

1,4-Cyclohexanedimethanol divinyl ether (CHDVE)

DODECYL VINYL ETHER

Di(ethylene glycol) divinyl ether (DEGDVE)

Particularly preferred compounds having one or more cationically polymerizable groups are selected from the compounds of formulae (J), (K), (M) and (N), more preferably from the compounds of formulae (K), (M) and (N).

The one or more curable compounds having a combination of at least one radically polymerizable carbon-carbon double bonds and at least one cationically polymerizable group(s) is not particularly limited. However, preferably, in such compound, the radically polymerizable carbon-carbon bonds are selected from (meth)acryloyl group(s) and (meth)acrylamide group(s), and the cationically polimerizable groups are selected from epoxide groups, oxetane groups, vinyl ether groups, aziridine groups, and azetidine groups.

More preferably, in such compound, the radically polymerizable carbon-carbon bond(s) is/are (meth)acrylamide group(s), and the cationically polymerizable groups are selected from vinyl ether groups, epoxide groups and oxetane groups. Most preferably, the cationically polymerizable group(s) is/are vinyl ether group(s) and/or epoxide group(s).

A compound having a combination of at least one radically polymerizable carbon-carbon double bonds and at least one cationically polymerizable group(s) may preferably be selected from the compounds of formula (P):

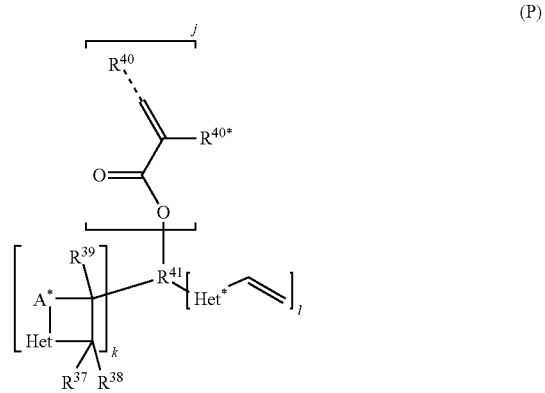

(P)

$R^{37}$, $R^{38}$, $R^{39}$ have the same meaning as $R^{29}$, $R^{29}$, $R^{39}$ defined above for formulae (J), (K) and (L), $R^{49}$, $R^{49*}$ have the same meaning as $R_{20}$ and $R_{20}^*$ defined above for formulae (A), (B) and (C), $R^{41}$ has the same meaning as $R_{23}$ defined above for formula (C), j is an integer of 0 to 6, preferably 1 to 3,
k is an integer of 0 to 6, preferably 0 to 3,
j is an integer of 0 to 6, preferably 0 to 3,
with the proviso that j+k+l≥2.

In formula (P), the dotted bond indicates that $R^{40}$ may be in (Z) or (E) configuration relative to CO.

In formula (P), $R^{37}$ and $R^{39}$ may cooperatively form a ring as defined above for $R^{29}$ and $R^{39}$ of formulae (G) and (H).

Most preferably, in compound (P), the radically polymerizable carbon-carbon bond(s) is/are (meth)acrylamide group(s), and the cationically polymerizable groups are vinyl ether groups.

It is preferred that in compound of formula (P), j=1 to 3, k=0 and j=1 to 3, $R^{40}$ is a hydrogen atom, $R^{40*}$ is a linear $C_{1-8}$ or branched or cyclic $C_{3-8}$ alkyl group, $R^{41}$ represents a $C_1$ to $C_{18}$ alkylene group which may contain 1 to 9 oxygen atoms, wherein the oxygen atoms may be contained such that an ethylene glycol moiety of formula $-[-O-CH_2-CH_2-]_n-$ with n=1 to 9 is formed.

A particularly preferred compound of formula (P) is 2-vinyloxyethoxyethyl methacrylate (VEEM) having the following structural formula:

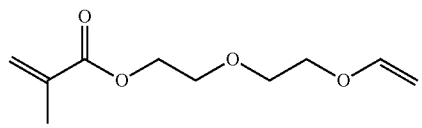

Preferably, the dental composition comprises a homogeneous phase comprising monomer combinations (x) and (y), (x) and (z), (y) and (z), or (x), (y) and (z), or comprising monomer (z), wherein (x) represents one or more compounds having at least one radically polymerizable carbon-carbon double bond;

(y) represents one or more compounds having at least one cationically polymerizable group;

(z) represents one or more compounds having a combination of at least one radically polymerizable carbon-carbon double bond and at least one cationically polymerizable group.

The term "homogeneous phase" means that monomer combinations (x) and (y), (x) and (z), (y) and (z), or (x), (y) and (z), or monomer(s) (z) are present in a single phase without detectable phase boundaries within the single phase. The term "monomer(s)" as used herein means a compound having a polymerizable group.

The term "interpenetrating polymer network (IPN)" as used herein means that two or more polymers are at least partially interlaced on a molecular scale, but not covalently bonded to each other and cannot be separated unless chemical bonds are broken. A mixture of two or more pre-formed polymers does not represent an IPN. If the two or more polymers of the IPN are formed of compounds having two or more polymerizable groups, then the IPN is according to the official IUPAC definition: "a polymer comprising two or more networks which are at least partially interlaced on a molecular scale, but not covalently bonded to each other and cannot be separated unless chemical bonds are broken". If one or more polymer(s) is/are formed of a compound having two or more polymerizable groups, and one or more polymer(s) is/are formed of a compound having a single polymerizable group, then the IPN is, according to the IUPAC definition, a so-called "semi-interpenetrating polymer network (SIPN): "a polymer comprising on or more networks and one or more linear or branched polymer(s) characterized by the penetration on a molecular scale of at least one of the networks by at least some of the linear of branched macromolecules". The present general definition of IPN includes the IPNs and SIPNs according to IUPAC definition, but also two or more linear or branched polymers which are at least partially interlaced on a molecular scale, but not covalently bonded to each other, and which cannot be separated unless chemical bonds are broken.

The radically polymerizable carbon-carbon double bonds and cationically polymerizable groups of monomers (x), (y) and (z) are not particularly limited. Preferably, radically polymerizable carbon-carbon double bonds are selected from carbon-carbon double bonds of (meth)acryloyl group(s) and a (meth)acrylamide group(s), preferably (meth)acryloyl group(s). Further, it is preferred that the cationically polymerizable groups are selected from epoxide groups, oxetane groups, vinyl ether groups, aziridine groups, and azetidine groups, preferably from epoxide groups, vinyl ether groups and oxetane groups, most preferably from epoxide groups and vinyl ether groups.

Preferably, the dental composition comprises a homogeneous phase comprising monomer combinations (x) and (y), (x) and (z), (y) and (z), or (x), (y) and (z), most preferably monomer combinations (x) and (y), (x) and (z), or (x), (y) and (z).

For example, monomer(s) (x) may be selected from compounds of formula (A), (B), (C), (D), (E), (F), (G) and (H), monomer(s) (y) may be selected from compounds of formula (J), (K), (L), (M), (N), (O), and monomer(s) (z) may be selected from compounds of formula (P).

Preferably, the homogeneous phase comprises one or more compound(s) (x) and/or (y) having two or more polymerizable carbon-carbon double bonds or cationically polymerizable groups, and/or one or more compounds) (z) having at least one polymerizable carbon-carbon double bonds and at least one cationically polymerizable groups. This provides for the formation of a crosslinked polymer network. The formation of a crosslinked polymer network is advantageous, since it imparts additional dimensional/mechanical stability to the IPN formed. More preferably, the homogeneous phase (a) comprises compound(s) (x) having two or more radically polymerizable carbon-carbon bonds selected from the group consisting of compounds of formulae (B) and (E), and/or compound(s) (y) having two or more cationically polymerizable groups selected from the group consisting of compounds of formulae (K) and (O), and/or compound(s) (z) having at least one radically polymerizable carbon-carbon double bond and at least one cationically polymerizable group selected from compounds of formula (P).

For a homogeneous phase comprising compound(s) (x), it is preferred that the homogeneous phase (a) contains components (x), (y) and (z) in a weight ratio (x)/((y)+(z)) of from 0.1 to 10.

The curable composition according to the present invention may comprise an initiator system. As an initiator system, any compound or system capable of initiating the polymerization of the one or more curable compounds may be used. The initiator system according to may be a photoinitiator system, a thermoinitiator system, a redox initiator system or a dual cure initiator system.

The term "dual cure initiator system" means an initiator system that contains a photoinitiator system and a redox initiator system or a photoinitiator system and a thermoinitiator system or a thermoinitiator system and a redox initiator system.

The term "triple cure initiator system" means an initiator system that contains a photoinitiator system and a redox initiator system and a thermal initiator system.

For example, a suitable photoinitiator system may be in the form of a singular, binary or tertiary system. A singular system may include a photoinitiator, a binary system may include a photoinitiator and an electron donor compound, and a tertiary system may include an iodonium, sulfonium or phosphonium salt, a photoinitiator, and an electron donor compound, as for example described in U.S. Pat. No. 5,545,676.

Suitable photoinitiators for the initiator system are monoketones and diketones that absorb some light within a range of about 400 nm to about 520 nm (preferably, about 450 nm to about 500 nm). Particularly suitable compounds include alpha diketones that have some light absorption within a range of about 400 nm to about 520 nm (even more preferably, about 450 to about 500 nm). Examples include camphor quinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate or dimethylamino benzonitrile.

A suitable photoinitiator system may also include phosphine oxides typically having a functional wavelength range of about 380 nm to about 1200 nm. Examples of phosphine oxide free radical initiators with a functional wavelength range of about 380 nm to about 450 nm include acyl and bisacyl phosphine oxides such as those described in U.S. Pat. Nos. 4,298,738, 4,324,744 US and U.S. Pat. No. 4,385, 109 and EP 0 173 567. Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis (2,6-dimethylphenyl)phosphonate, and 2,4,6-trimethylbenzoylethoxyphenylphosphine oxide. Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X). Typically, the phosphine oxide initiator is present in the composition in catalytically effective amounts, such as from 0.1 percent by weight to 5.0 percent by weight, based on the total weight of the composition.

Tertiary amine reducing agents may be used in combination with an acylphosphine oxide Examples of suitable aromatic tertiary amine include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, 4-N,N-dimethylaminobenzoic acid ethyl ester, 4-N,N-dimethylaminobenzoic acid methyl ester, 4-N,N-dimethylaminobenzoic acid n-butoxyethyl ester, 4-N,N-dimethylaminobenzoic acid 2-(methacryloyloxy) ethyl ester, 4-N,N-dimethylaminobenzophenone ethyl 4-(N,N-dimethylamino) benzoate and N,N-dimethylaminoethyl methacrylate. Examples of an aliphatic tertiary amine include trimethylamine, triethylamine, N-methyldiethanolamine, N-ethyldiethanolamine, N-n-butyldiethanolamine, N-lauryldiethanolamine, triethanolamine, 2-(dimethylamino) ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

The amine reducing agent may be present in the composition in an amount from 0.1 percent by weight to 5.0 percent by weight, based on the total weight of the composition.

Apart from the above mentioned photoinitiators, photoinitiators may be applied having the following formula (III):

$$X^P\text{---}R^P \quad (III)$$

wherein
$X^P$ is a group of the following formula (IV):

(IV)

wherein
M is Si or Ge;
$R^6$ represents a substituted or unsubstituted hydrocarbyl or hydrocarbylcarbonyl group;
$R^7$ represents a substituted or unsubstituted hydrocarbyl or hydrocarbylcarbonyl group;
$R^8$ represents a substituted or unsubstituted hydrocarbyl group; and
$R^P$ a) has the same meaning as $X^P$, whereby the compound of formula (III) may be symmetrical or unsymmetrical; or
b) is a group of the following formula (V):

(V)

wherein
$Y^P$ represents a single bond, an oxygen atom or a group NR', wherein R' represents a substituted or unsubstituted hydrocarbyl group;
$R^9$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group; or
when M is Si, $R^P$ may be a substituted or unsubstituted hydrocarbyl group.

In formula (III), the term "substituted" as used herein means that $R^6$, $R^7$, $R^8$, $R^9$ and R' may be substituted by a substituent selected from the group consisting of halogen atoms, a nitro group, a cyano group, a hydroxy group, an amino group, $C_{1-6}$ alkyl groups, $C_{1-6}$ alkoxy groups and a —$NR^xR^y$ group wherein $R^x$ and $R^y$ independently from each other represent a $C_{1-6}$ alkyl group. Here, illustrative of the halogen atoms can be fluorine, chlorine, bromine and iodine. The $C_{1-6}$ alkyl groups are, for example, methyl, ethyl, n-propyl, isopropyl and n-butyl. Illustrative of the $C_{1-6}$ alkoxy groups are, for example, methoxy, ethoxy and propoxy. The alkyl moieties in these substituents may be linear, branched or cyclic. Preferably, the substituent is selected from a chlorine atom, a nitro group, a $C_{1-4}$ alkoxy group and a —$NR^xR^y$ group wherein $R^x$ and $R^y$ independently from each other represent a $C_{1-4}$ alkyl group.

If $R^6$, $R^7$ and $R^8$ are substituted, then it is preferred that they are substituted with 1 to 3 substituents, more preferably with 1 substituent.

In the compound of formula (III), moieties $R^6$, $R^7$ and $R^8$ may be defined as follows:

$R^6$ and $R^7$ independently from each other represent a substituted or unsubstituted hydrocarbyl or hydrocarbylcarbonyl group, and $R^8$ represents a substituted or unsubstituted hydrocarbyl group.

The hydrocarbyl group may be an alkyl group, a cycloalkyl group, a cycloalkylalkyl group, an arylalkyl group or an aryl group.

An alkyl group may be straight-chain or branched $C_{1-20}$ alkyl group, typically a $C_{1-8}$ alkyl group. Examples for a $C_{1-6}$ alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl.

A cycloalkyl group may be a $C_{3-20}$ cycloalkyl group, typically a $C_{1-8}$ cycloalkyl group. Examples of the cycloalkyl group can include those having 3 to 6 carbon atoms, for example, cyclopropyl, cyclobutyl, cyclopentyl and cyclohexyl.

A cycloalkylalkyl group may have 4 to 20 carbon atoms and may include a combination of a linear or branched alkyl group having 1 to 6 carbon atoms and a cycloalkyl group having 3 to 14 carbon atoms. Examples of the cycloalkylalkyl(-) group can for example, include methylcyclopropyl (-) methylcyclobutyl(-), methylcyclopentyl(-), methylcyclohexyl(-), ethylcyclopropyl(-), ethylcyclobutyl(-), ethylcyclopentyl(-), ethylcyclohexyl(-), propylcyclopropyl (-), propylcyclobutyl(-), propylcyclopentyl(-), propylcyclohexyl(-).

An arylalkyl(-) group may be a $C_{7-20}$ arylalkyl(-) group, typically a combination of a linear or branched alkyl group having 1 to 6 carbon atoms and an aryl(-) group having 6 to 10 carbon atoms. Specific examples of an arylalkyl(-) group are a benzyl(-) group or a phenylethyl(-) group.

An aryl group can include aryl groups having 6 to 10 carbon atoms. Examples of the aryl group are phenyl and naphtyl.

The hydrocarbylcarbonyl groups of $R^6$ and $R^7$ represent acyl groups ($R_{org}$—(C=O)—) in which the organic residue $R_{org}$ is a hydrocarbyl residue as defined above.

In the compound of formula (III), $R^P$ may have the same meaning as X, whereby the compound of formula (III) may be symmetrical or unsymmetrical. Alternatively, $R^P$ may represent a substituted or unsubstituted hydrocarbyl group, or a group of formula (V). Preferably, if $R^P$ has the same meaning as X, then compound of formula (III) is unsymmetrical. If $R^P$ represents a substituted or unsubstituted hydrocarbyl group, then the hydrocarbyl group has the same meaning as defined above for $R^6$ and is independently selected therefrom.

In the group of formula (V) of compound of formula (III), $R^6$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group.

If $R^9$ of formula (V) is a trihydrocarbylsilyigroup, a mono(hydrocarbylcarbonyl)-dihydrocarbylsilyl group or a di(hydrocarbylcarbonyl)monohydrocarbylsilyl group, each of the hydrocarbyl and hydrocarbylcarbonyl groups has the same meaning as defined for $R^6$, $R^7$ and $R^8$ and is independently selected therefrom.

In formula (V), R' has the same meaning as defined for $R^8$ and is independently selected therefrom.

If M is Si in compound of formula (III), $R^P$ may be also be a substituted or unsubstituted hydrocarbyl group, wherein the hydrocarbyl group has the same meaning as defined above for $R^8$ and is independently selected therefrom.

For example, compounds of formula (III) wherein $R^P$ has the same meaning as $X^P$ and which are symmetrical may be have the following structural formulae:

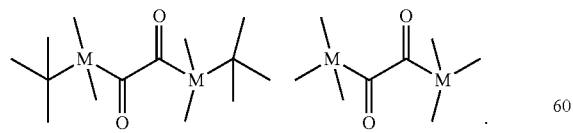

For example, compounds of formula (III) wherein $R^P$ represents a group of formula (V) wherein $Y^P$ is a bond, an oxygen atom or a NR' group, and $R^9$ represents a substituted or unsubstituted hydrocarbyl group may have the following structural formulae:

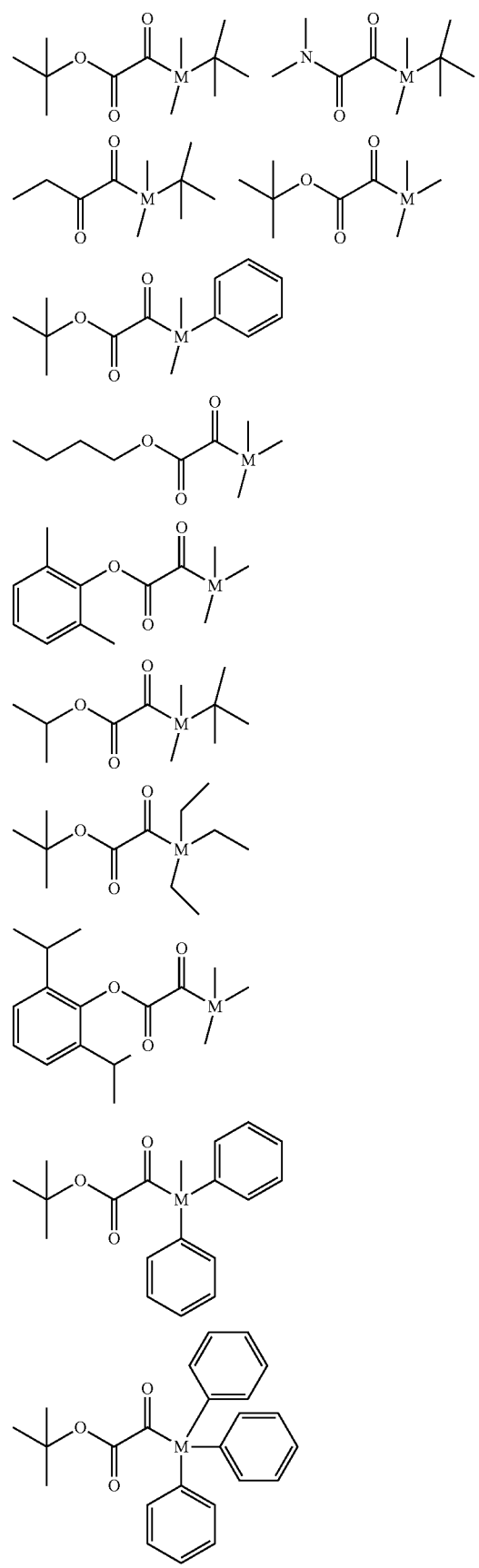

-continued

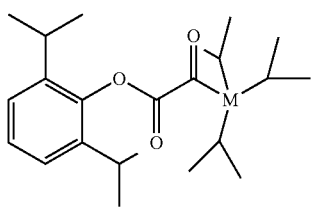

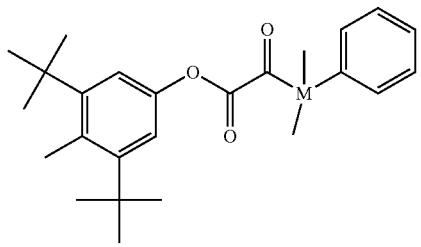

For example, compounds of formula (III) wherein $R^P$ represents a group of formula (V) wherein $R^9$ represents a trihydrocarbylsilyl group have the following structural formulae:

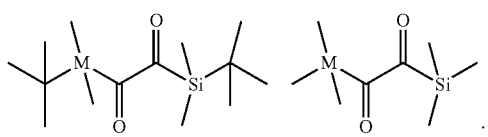

For example, compounds of formula (III) wherein M is Si and $R^P$ represents a substituted or unsubstituted hydrocarbyl group, may have the following structural formulae:

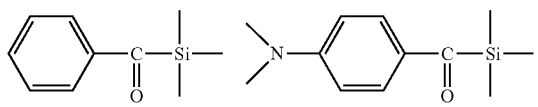

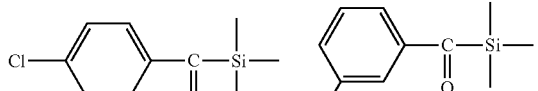

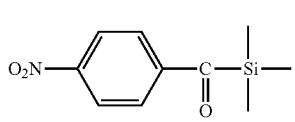

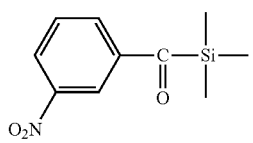

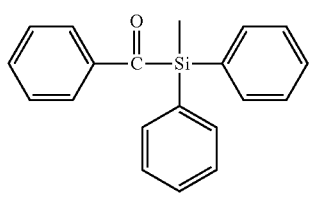

-continued

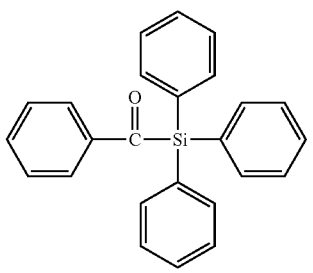

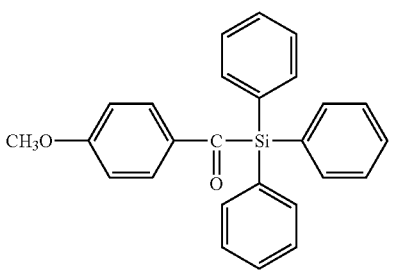

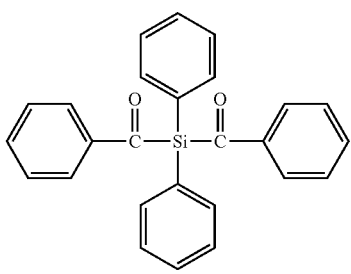

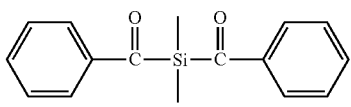

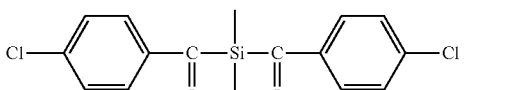

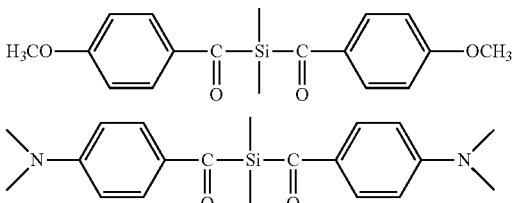

Preferably, compound of formula (III) is selected from the group consisting of:

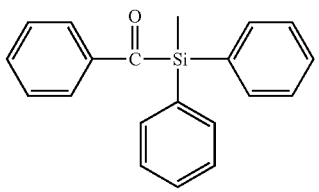

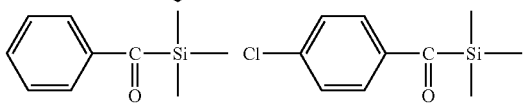

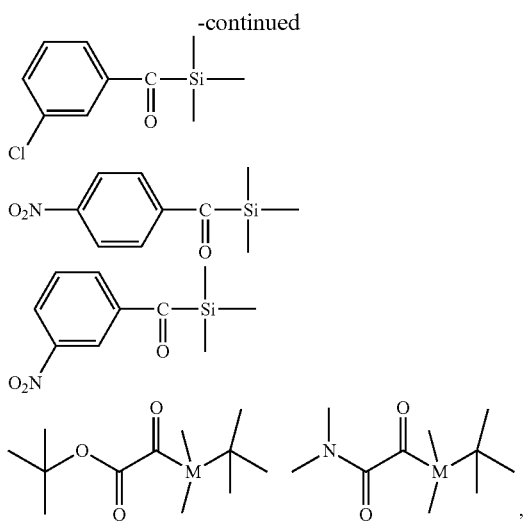

wherein compounds of formula (III) with M=Si are particularly preferred.

Most preferably, compound of formula (III) is selected from the group consisting of:

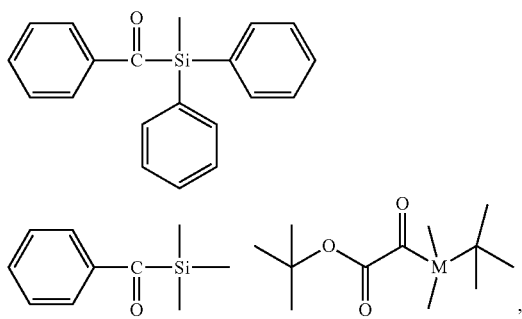

wherein it is particularly preferred that M=Si.

The compound of the formula (III) may be a known compound which is commercially available or a may be prepared according to published procedures.

The photoinitiator system may further comprise diaryl iodonium salts, triaryl sulfonium salts and tetraaryl or tetraalkyl phosphonium salts. These salts may serve as a coinitiator for improving the polymerization performance of the photoinitiator, but they may also serve as an initiator for cationic polymerization.

For example, diaryl iodonium salt may be selected from the group consisting of (4-methylphenyl)[4-(2-methylpropyl) phenyl] iodonium hexafluoroantimonate, include (4-methylphenyl)[4-(2-methylpropyl) phenyl] iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl) iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, DPI hexafluorophosphate, Me2-DPI hexafluorophosphate; DPI hexafluoroarsenate, di(4-phenoxyphenyl)iodonium tetrafluoroborat, phenyl-2-thienyliodonium hexafluorophosphate, 3,5-dimethylpyrazolyl-4-phenyliodonium hexafluorophosphate, DPI hexafluoroantimonate, 2,2'-DPI tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl) iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, and DPI hexafluorophosphate.

Particularly preferred iodonium compounds include diphenyliodonium (DPI) hexafluorophosphate, di(4-methylphenyl)iodonium (Me2-DPI) hexafluorophosphate, diaryliodonium hexafluoroantimonate, (4-methylphenyl)[4-(2-methylpropyl) phenyl] iodonium hexafluoroantimonate, (4-methylphenyl)[4-(2-methylpropyl)phenyl]iodonium hexafluorophosphate (Irgacure® 250, commercial product available from BASF SE), (4-methylphenyl)[4-(2-methylpropyl) phenyl] iodonium tetrafluoroborate, 4-octyloxyphenyl phenyliodonium hexafluoroantimonate, 4-(2-hydroxytetradecyloxyphenyl)phenyliodonium hexafluoroantimonate, and 4-isopropyl-4'-methyldiphenyliodonium borate.

According to a particularly preferred embodiment, the iodonium compound is DPI hexafluorophosphate and/or 4-isopropyl-4'-methyldiphenyliodonium tetrakis(pentafluorophenyl) borate.

A preferred triaryl sulfonium salt is S-(phenyl)thianthrenium hexafluorophosphate of the following formula:

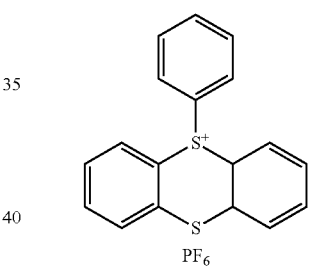

Particularly preferred phosphonium salts are the tetraalkyl phosphonium salts tetrakis-(hydroxymethyl)-phosphonium (THP) salt or a tetrakis-(hydroxymethyl)-phosphonium hydroxide (THPOH) salt, wherein the anion of the tetraalkyl phosphonium salt is selected from the group consisting of formate, acetate, phosphate, sulphate, fluoride, chloride, bromide and iodide.

A particularly preferred photoinitiator system in the range of visible light comprises a photoinitiator of formula (III), optionally in addition with camphor quinone, in combination with a diaryl iodonium salt, triaryl sulfonium salt or a tetraaryl or tetraalkyl phosphonium salt as described above.

A preferred photoinitiator system in the near-UV range (300-400 nm) comprises phenylphosphinoxide compounds, preferably 2,4,6-trimethylbenzoyldiphenylphosphine oxide and/or bis(2,4,6-trimethylbenzoyl)phenylphosphine oxide.

A suitable thermoinitiator system comprises at least one compound that produces free radicals, capable of initiating polymerization of the polymerizable group(s) of polymerizable compound(s) (ii) or further polymerizable compounds in the presence of heat. Typical thermoinitiators comprise azo-compounds like 2,2'-azobis(2-methylpropionitrile), 2,2'-azobis(4-methoxy-2,4-dimethylvaleronitrile), 4-cyano-4-(2-cyano-5-hydroxy-5-oxopentan-2-yl)diazenylpentanoic acid, 2,2'-azobis(2,4-dimethylvaleronitrile), 1,1'-azobis(cyclohexane-1-carbonitrile), 2,2'-azobis[2-methyl-N-(2-hydroxyethyl)propionamide], 2,2'-azobis (N-butyl-2-methylpropionamide), 2,2'-azobis[2-(2-imidazolin-2-yl)propane] dihydrochloride, 2,2'-azobis[2-(2-imidazolin-2-yl)propane], or dimethyl 2,2'-azobis(2-methylpropionate), organic peroxides like dibenzoyl peroxide, dicumyl peroxide or inorganic peroxides like potassium persulfate or sodium persulfate.

A suitable redox initiator system comprises reducing and oxidizing agents, which produce free-radicals capable of initiating polymerization of the polymerizable group(s) of polymerizable compound(s) (ii) or further polymerizable compounds independent from the presence of light. The reducing and oxidizing agents are selected so that the initiator system (iii) is sufficiently storage-stable and free of undesirable colorization to permit storage and use under typical dental conditions. Moreover, the reducing and oxidizing agents are selected so that the initiator system (iii) is sufficiently miscible with the resin system to permit dissolution of the initiator system in the composition.

Useful reducing agents include ascorbic acid, ascorbic acid derivatives, and metal complexed ascorbic acid compounds as described in U.S. Pat. No. 5,501,727; amines, namely tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine, salts of a dithionite or sulfite anion, and mixtures thereof.

Suitable oxidizing agents include persulfuric acid and salts thereof, such as ammonium, sodium, potassium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof. One or more different oxidizing agents or one or more different reducing agent may be used in the initiator system. Small quantities of transition metal compounds may also be added to accelerate the rate of redox cure. The reducing and oxidizing agents are present in amounts sufficient to permit an adequate free-radical reaction rate.

The reducing or oxidizing agents may be microencapsulated for enhancing shelf stability of the composition, and if necessary permitting packaging the reducing and oxidizing agents together (U.S. Pat. No. 5,154,762). Appropriate selection of an encapsulant may allow combination of the oxidizing and reducing agents and even of an acid-functional component and optional filler in a storage-stable state. Moreover, appropriate selection of a water-insoluble encapsulant allows combination of the reducing and oxidizing agents with the particulate reactive glass and water in a storage-stable state.

The amount of active species of the initiator system (iii) is not particularly limited. Suitably, the amount of photoinitiator in the initiator system (iii) is in the range of from 0.001 to 5 mol % based on the total amount of the one or more polymerizable compounds (ii) or further polymerizable compounds described below.

Further Optional Components

The dental composition according to the present invention may, besides of the above described optional components, comprise additional optional components.

For example, the curable composition used according to the present invention may comprise suitable solvents. These solvents may be selected from water, alcohols such as methanol, ethanol, propanol (n-, 1-), butanol (n-, iso-, tert.-), and ketones such as acetone or the like. The dental composition of the present invention may comprise the solvent in an amount of 5 to 75 percent by weight based on the total weight of the composition.

The filler of the curable composition according to the present invention may optionally comprise a further filler other than the glass flakes and the structural filler. The further filler may be selected from nanofillers having a particle diameter $D_{3,50}$ of the primary particles of from 5 to 100 nm. Preferably, the further filler is silanated. Suitable silanated nanofillers are disclosed in EP0969789. A specific example of a silanated nanofiller is Cab-O-Sil TS720 (Cabot Corporation). The further filler may be contained in the filler of the curable composition in an amount of up to 50 percent by weight, more preferably 0.1 to 20 percent, still more preferably 0.5 to 5 percent by weight based on the total weight of the curable composition.

The additive manufacturing process of the present invention further comprises a step of controlling an apparatus to form an object by using the curable composition, whereby the curable composition passes a discharge orifice having a minimum diameter $\Phi_{min}$. The discharge orifice may form part of a nozzle. In particular, the nozzle may form part of a cartridge for storing and discharging the curable material. Alternatively, the nozzle may form part of the apparatus. The nozzle may be a member protruding from the cartridge body or apparatus or be an orifice in the wall of the cartridge body or storage compartment of the apparatus without any protrusion beyond the wall of the cartridge or storage compartment.

According to a preferred embodiment, the minimum diameter of the discharge orifice is in the range of from 10 to 1500 μm. More preferably, $\Phi_{min}$ is in the range of from 30 to 300 μm in order to provide a high-resolution print.

The length of the nozzle may be in the range of from 0.1 to 20 mm.

According to a preferred embodiment, the additive manufacturing process is selected from a jetting process and an extrusion process. The apparatus may be a 3D printer comprising a printer unit, which at least comprises a printer head for printing with the curable composition of the present invention as the 3D printable material. Optionally, the 3D printer unit may comprise a material dosing unit configured to mix a two-part curable composition.

The control of the apparatus may be based on a 3D printable model stored in a design file sent from a design module, such as a workstation, to the apparatus. The design file provides a digital representation of the dental appliance that is usable by the apparatus to generate the physical dental appliance. 3D printable models can be saved in the stereolithography file format (STL) storing data based on triangulations of CAD models. A newer CAD file format, the Additive Manufacturing File format (AMF), wherein information is stored using curved triangulations may also be used.

The dental appliance can be fabricated chairside using one or more of the available additive manufacturing techniques wherein the curable composition passes a discharge orifice having a minimum diameter $\Phi_{min}$. The additive manufacturing techniques may include 3D printing or other 3D printing technologies including extrusion deposition. Although, the design for the dental appliance can be realized using the apparatus located at the dental treatment office, the design for the dental restorative product may also be sent, e.g., via the Internet, other computer network to a secure server, or mail using an electronic medium, to another facility to fabricate the dental restorative product.

The additive manufacturing process of the present invention may further comprise the step of curing the curable composition. The curing may be carried out after each layer has been formed. Alternatively, the curing may be carried out after two or more layers of the curable composition is applied.

According to a preferred embodiment, the process according to the present invention may further comprise a final curing step wherein the object is cured for an extended period of time by the application of light and/or heat.

In the additive manufacturing method of the present invention, the ratio of the minimum diameter of the discharge orifice to the diameter $D_{3,99}$ of the glassflakes ($\Phi_{min}/D_{3,99}$) is in the range of 2 to less than 10.

According to a preferred embodiment, the process according to the present invention is for preparing a dental appliance, wherein the object is preferably a single unit permanent dental restoration, wherein the object is preferably at least a portion of a dental crown, inlay, onlay or veneer.

The present invention also provides a cartridge for a 3D printer, which contains a curable dental composition, the cartridge having a discharge orifice for ejecting or extruding the curable composition during 3D printing wherein the ratio of the minimum diameter of the discharge orifice $\Phi_{min}$ to the diameter $D_{3,99}$ of the glassflakes as determined by light scattering ($\Phi_{min}/D_{3,99}$) is less than 10.

The cartridge may have a single barrel or at least two elongated barrels. The barrels are used to store and dispense at least a component of the curable composition. The cartridge may include a dispensing tip containing a static mixing element for mixing the components and then dispensing the mixed composition through the discharge orifice.

A cartridge according to the present invention is for extruding or ejecting a one-part curable composition or a multi-part curable composition, preferably a two-part composition. In one embodiment, the cartridge includes a cartridge body having a double barrel structure. The first elongated barrel is used for storing and discharging a first component of the curable composition. The first barrel has an opening for receiving a first plunger rod and an exit port for discharging the first component. The second elongated barrel is used for storing and discharging a second component of the curable composition. The second barrel has an opening for receiving a second plunger rod and an exit port for discharging the second component.

The cartridge body may include a dispensing tip for receiving the first and second components of the curable composition. The dispensing tip then delivers the composition to the discharge orifice. The dispensing tip may further be outfitted with a static mixing element, which combines and mixes the components of the curable composition. The mixed composition is then dispensed through the discharge orifice of the nozzle of the dispensing tip.

The cartridge may have more than two barrels and can be used to dispense a multi-component curable composition. For example, the cartridge may have three (3) or four (4) barrels for dispensing a three or four component curable composition.

The present invention also provides a kit-of-parts comprising a plurality of cartridges of the invention, each cartridge containing a dental composition and optionally a support material, whereby the cartridge is marked to distinguish the dental composition from a support material or to identify a property of the cured dental composition and/or support material, which property is preferably selected from the color, and/or opacity.

The present invention will now be further described based on the following examples.

EXAMPLES

Milling of Glassflakes by Means of Pearl Mill:

The grinding container of the mill (Dyno-mill Multi Lab, Willy A. Bachofen AG Maschinenfabrik) was filled with 450 mL grinding beads (soda-lime glass, 0.75-1 mm). In a storage tank 100 g ECR glassflakes GF350 nmM (from Glassflake Ltd., Leeds, England) without surface functionalization were dispersed in 1.5 L water. A homogeneous dispersion was maintained by continuous stirring. The dispersion was pumped by a peristaltic pump into the grinding container and returned from the mill outlet into the storage tank. Milling was stopped once the particle diameter $D_{3,50}$ and $D_{3,99}$ reached the desired values.

Washing of Glassflakes:

When adding unwashed glassflakes into a dental composition, greyish pastes were obtained. For better aesthetical results, the glassflakes may be washed prior to coating. For washing, the glassflakes may be stirred in twice the amount of 2.5% hydrochloric acid for half an hour, and then filtered off and washed with about the twentyfold amount of water during filtration. Finally, the glassflakes may be dried at 80° C. for about 16 h.

Coating of Glassflakes with a Silane:

Milled glassflakes were dispersed in about five times the amount of 2-propanol and stirred for 1 h. During stirring, the suspension was treated with ultrasound. 3 wt-% of 3-(trimethoxysilyl)propyl methacrylate (related to the glassflake amount) were added drop-wise to the suspension. Subsequently, the solvent was removed in vacuo, and the residue was dried at 80° C. for about 16 h. The coated glassflakes were sieved through a 180 μm sieve for deaggregation. In a beaker containing about 50 mL water, a portion of about 50 mg of the coated glassflakes was placed on the surface, whereby the coated glassflakes stay afloat, which indicates that the glassflakes have been coated with hydrophobic 3-(trimethoxysilyl)propyl methacrylate.

Paste Preparation:

4.05 g silanized glassflakes (GF350 nmM, $D_{3,50}$=12 μm; $D_{3,99}$<43 μm), 10.65 g Type 3 barium glass (SDI, $D_{3,50}$=0.6 μm) and 0.3 g Cab-O-Sil TS720 (Cabot Corporation) were compounded with 10.00 g of a photocurable methacrylate-based monomer mixture as it is known in the art. To improve extrudability of the paste, the material was treated using an EXAKT model 80E three-roll-mill. The extrusion force (EF) of the paste from a cartridge with a nozzle having an inner diameter of 600 μm and a length of 11 mm, was investigated using a Zwick RetroLine tensile testing machine. For the given paste, cartridge extrusion force at room temperature is 24 N. Flexural strength (FS) and E-modulus of the paste was investigated using the Zwick as well. For the present paste, FS is 113 MPa, E-modulus is 6.8 GPa.

Particle Size Analysis:

Method for measuring the median particle diameter ($D_{3,50}$) and the $D_{3,99}$ of the glassflakes:

A small amount of glassflakes was directly added into the measuring cell of a Malvern Mastersizer 3000, containing 800 mL of water and being equipped with a stirrer set to 2200 U/min and an ultrasound probe set to 80%. The actual amount of glassflakes added here was depending on the laser shadowing detected by the measuring device. The amount of added glassflakes lead to laser shadowing of 8-15%. The median particle diameter was measured after applying ultrasound from the ultrasound probe in the measurement cell under stirring for 2 minutes. Ultrasound was applied to break up loosely aggregated/layered glassflakes.

The following parameters were defined in the Malvern Mastersizer 3000 software:

| | |
|---|---|
| Refractive Index of the Particles | 1.530 |
| Particle Density | 2.00 g/cm$^3$ |
| Analysis Model | Universal |
| Scattering Model | Mie |
| Dispersing Medium | Water |
| Refractive Index | 1.330 |
| Ultrasonic Strength | 80% |
| Ultrasonic Duration (before measurement) | 2 min |
| Stirrer RPM | 2200 |
| Laser Shadowing | 8-15% |
| Laser Intensity | ≥75% |
| Size Distribution | Volumetric |

The results are shown in FIG. 1.

The invention claimed is:

1. An additive manufacturing process comprising:
   (a) providing a curable composition comprising:
      (i) a filler comprising glassflakes having a diameter $D_{3,99}$ as determined by light scattering in the range of from 5 to 150 µm; and
      (ii) one or more curable compounds;
   (b) controlling an apparatus to form an object by using the curable composition, whereby the curable composition passes a discharge orifice having a minimum diameter $\Phi_{min}$,
   wherein the ratio of the minimum diameter of the discharge orifice to the diameter $D_{3,99}$ of the glassflakes ($\Phi_{min}/D_{3,99}$) is in the range of 2 to less than 10; and
   wherein the median diameter $D_{3,50}$ of the glassflakes is larger than the average thickness of the glassflakes.

2. The process according to claim 1, further comprising the step of
   (c) curing the curable composition.

3. The process according to claim 1, which is for preparing a dental appliance.

4. The process according to claim 1, wherein the filler of the curable composition further comprises a structural filler having a $D_{3,99}$ particle diameter of less than 5 µm.

5. The process according to claim 1, wherein the curable composition further comprises a photoinitiator system and/or a thermoinitiator system and/or a redox initiator system.

6. The process according to claim 1, wherein the additive manufacturing process is selected from a jetting process and an extrusion process.

7. The process according to claim 1, wherein the discharge orifice forms part of a nozzle.

8. The process according to claim 7, wherein the nozzle forms part of a cartridge for storing and discharging the curable material, or wherein the nozzle forms part of the apparatus.

9. The process according to claim 1, wherein the minimum diameter of the discharge orifice is in the range of from 10 to 1500 µm.

10. The process according to claim 1, wherein the glassflakes have a median particle diameter $D_{3,50}$ of 3 to 25 µm as determined by light scattering, and/or wherein the glassflakes have an aspect ratio (median particle diameter $D_{3,50}$/average thickness) of at least 10:1.

11. The process according to claim 1, which contains 1 to 85 percent by weight of the filler (i) based on the total weight of the composition.

12. The process according to claim 4, wherein the ratio of the weight of structural filler and the weight of the glassflakes in the dental composition of the cartridge is in the range of from 80:1 to 1:80.

13. The process according to claim 3, wherein the dental appliance is a single unit permanent dental restoration selected from at least a portion of a dental crown, inlay, onlay or veneer.

14. The process according to claim 4, wherein the refractive index of the glassflakes and the structural filler is in the range of 1.40 to 1.60.

15. The process according to claim 1, which contains the glassflakes in an amount of from 0.5 to 83 percent by weight based on the total weight of the composition.

\* \* \* \* \*